(12) United States Patent
Donner

(10) Patent No.: US 10,517,734 B2
(45) Date of Patent: Dec. 31, 2019

(54) SINGLE IMPLANT SACROILIAC JOINT FUSION SYSTEM USING A POSTERIOR APPROACH FOR MINIMAL TISSUE DISRUPTION

(71) Applicant: JCBD, LLC, Fort Collins, CO (US)

(72) Inventor: Edward Jeffrey Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 16/041,372

(22) Filed: Jul. 20, 2018

(65) Prior Publication Data

US 2018/0325676 A1    Nov. 15, 2018

Related U.S. Application Data

(60) Continuation of application No. 15/992,987, filed on May 30, 2018, now Pat. No. 10,130,477, which is a
(Continued)

(51) Int. Cl.
*A61F 2/30* (2006.01)
*A61F 2/44* (2006.01)
(Continued)

(52) U.S. Cl.
CPC ...... *A61F 2/30988* (2013.01); *A61B 17/1626* (2013.01); *A61B 17/1739* (2013.01);
(Continued)

(58) Field of Classification Search
CPC ....... A61F 2/30988; A61F 2002/30995; A61B 17/7055
See application file for complete search history.

(56) References Cited

U.S. PATENT DOCUMENTS 4,805,602 A    2/1989    Puno
5,662,652 A    9/1997    Schafer
(Continued)

OTHER PUBLICATIONS

Amendment Under 1.312, U.S. Appl. No. 15/828,622, dated Oct. 26, 2018.
(Continued)

*Primary Examiner* — Christian A Sevilla
(74) *Attorney, Agent, or Firm* — Polsinelli PC; Joshua J. Pranckun; Samuel Wade Johnson

(57) ABSTRACT

A method for preparing a sacroiliac joint for stabilization which may include approaching a posterior aspect of the sacroiliac joint inferior to a PSIS with a defect-creating tool assembly, creating a defect in the sacrum and the ilium defined by at least one noncircular cross-sectional shape, delivering an implant having a body with a length extending between proximal and distal ends, the body including at least one cylindrical body with a longitudinal axis and an opening at the proximal end aligned with the longitudinal axis of the cylindrical body, a pattern of openings spaced along the cylindrical body and a planar member coupled with and extending along the cylindrical body. The implant may be implanted with the length generally following a plane of the sacroiliac joint such that it is advanced from a generally posterior to anterior approach while the body of the implant bridges the joint.

42 Claims, 19 Drawing Sheets

Related U.S. Application Data continuation of application No. 15/910,753, filed on Mar. 2, 2018, now Pat. No. 10,058,430, which is a continuation of application No. 15/828,677, filed on Dec. 1, 2017, now Pat. No. 9,931,212, which is a continuation of application No. 15/061,524, filed on Mar. 4, 2016, now Pat. No. 9,833,320, which is a division of application No. 13/946,790, filed on Jul. 19, 2013, now Pat. No. 9,333,090, and a continuation-in-part of application No. 13/475,695, filed on May 18, 2012, now Pat. No. 9,381,045, which is a continuation-in-part of application No. 13/236,411, filed on Sep. 19, 2011, now Pat. No. 9,017,407, which is a continuation-in-part of application No. 12/998,712, filed as application No. PCT/US2011/000070 on Jan. 13, 2011, now Pat. No. 8,979,928, application No. 16/041,372, which is a continuation-in-part of application No. 14/344,876, filed as application No. PCT/US2012/055892 on Sep. 18, 2012, now Pat. No. 10,034,676, which is a continuation-in-part of application No. 13/475,695, filed on May 18, 2012, now Pat. No. 9,381,045, which is a continuation-in-part of application No. 13/236,411, filed on Sep. 19, 2011, now Pat. No. 9,017,407, which is a continuation-in-part of application No. 12/998,712, filed as application No. PCT/US2011/000070 on Jan. 13, 2011, now Pat. No. 8,979,928.

(60) Provisional application No. 61/335,947, filed on Jan. 13, 2010, provisional application No. 61/674,277, filed on Jul. 20, 2012, provisional application No. 61/674,130, filed on Jul. 20, 2012, provisional application No. 61/800,120, filed on Mar. 15, 2013.

(51) Int. Cl.
| | | |
|---|---|---|
| *A61B 17/16* | (2006.01) | |
| *A61B 17/17* | (2006.01) | |
| *A61F 2/46* | (2006.01) | |
| *A61B 17/70* | (2006.01) | |
| *B33Y 80/00* | (2015.01) | |
| *A61B 17/02* | (2006.01) | |
| *A61B 17/86* | (2006.01) | |
| *A61B 17/00* | (2006.01) | |

(52) U.S. Cl.
CPC ...... *A61B 17/1757* (2013.01); *A61B 17/7055* (2013.01); *A61B 17/7074* (2013.01); *A61F 2/4455* (2013.01); *A61F 2/4611* (2013.01); *A61B 17/025* (2013.01); *A61B 17/7043* (2013.01); *A61B 17/8645* (2013.01); *A61B 2017/0046* (2013.01); *A61F 2002/304* (2013.01); *A61F 2002/3055* (2013.01); *A61F 2002/30163* (2013.01); *A61F 2002/30382* (2013.01); *A61F 2002/30401* (2013.01); *A61F 2002/30428* (2013.01); *A61F 2002/30484* (2013.01); *A61F 2002/30504* (2013.01); *A61F 2002/30509* (2013.01); *A61F 2002/30579* (2013.01); *A61F 2002/30601* (2013.01); *A61F 2002/30622* (2013.01); *A61F 2002/30774* (2013.01); *A61F 2002/30828* (2013.01); *A61F 2002/30995* (2013.01); *A61F 2002/4623* (2013.01); *A61F 2002/4687* (2013.01); *A61F 2310/00017* (2013.01); *A61F 2310/00023* (2013.01); *A61F 2310/00179* (2013.01); *A61F 2310/00359* (2013.01); *B33Y 80/00* (2014.12)

(56) References Cited

U.S. PATENT DOCUMENTS

| | | | |
|---|---|---|---|
| 6,053,916 A * | 4/2000 | Moore | A61F 2/30988 606/86 R |
| 7,935,116 B2 | 5/2011 | Michelson | |
| 7,942,903 B2 | 5/2011 | Moskowitz et al. | |
| 9,039,765 B2 | 5/2015 | Trieu | |
| 9,149,286 B1 | 10/2015 | Greenhalgh | |
| 9,452,065 B1 | 9/2016 | Lawson | |
| 9,474,538 B2 | 10/2016 | Foley | |
| 9,486,264 B2 | 11/2016 | Reiley | |
| 9,936,983 B2 | 4/2018 | Mesiwala | |
| 9,949,843 B2 | 4/2018 | Reiley | |
| 10,130,477 B2 | 11/2018 | Donner et al. | |
| 10,136,995 B2 | 11/2018 | Donner et al. | |
| 10,179,014 B1 | 1/2019 | Menmuir | |
| 10,321,945 B2 | 6/2019 | Schifano | |
| 2002/0103487 A1 | 8/2002 | Errico | |
| 2005/0261775 A1 | 11/2005 | Baum | |
| 2006/0036251 A1 | 2/2006 | Reiley | |
| 2007/0299445 A1 | 12/2007 | Shadduck | |
| 2009/0062914 A1 | 3/2009 | Marino | |
| 2009/0099659 A1 | 4/2009 | Oh | |
| 2009/0204215 A1 | 8/2009 | McClintock | |
| 2009/0216238 A1 * | 8/2009 | Stark | A61B 17/025 606/96 |
| 2009/0281579 A1 | 11/2009 | Weaver | |
| 2010/0145397 A1 | 6/2010 | Overes | |
| 2010/0168798 A1 | 7/2010 | Clineff | |
| 2010/0168861 A1 | 7/2010 | Yundt | |
| 2010/0191088 A1 | 7/2010 | Anderson | |
| 2010/0191100 A1 | 7/2010 | Anderson | |
| 2010/0204796 A1 * | 8/2010 | Bae | A61B 17/846 623/17.16 |
| 2010/0217086 A1 | 8/2010 | Deshmukh | |
| 2011/0213221 A1 | 9/2011 | Roche | |
| 2011/0230968 A1 | 9/2011 | Perisic | |
| 2012/0065548 A1 | 3/2012 | Morgan | |
| 2013/0035724 A1 | 2/2013 | Fitzpatrick | |
| 2013/0144393 A1 | 6/2013 | Mutchler | |
| 2013/0173004 A1 | 7/2013 | Greenhalgh | |
| 2013/0238093 A1 | 9/2013 | Mauldin | |
| 2013/0245763 A1 | 9/2013 | Mauldin | |
| 2013/0296953 A1 | 11/2013 | Mauldin | |
| 2014/0207240 A1 | 7/2014 | Stoffman | |
| 2014/0277463 A1 | 9/2014 | Yerby | |
| 2015/0080972 A1 | 3/2015 | Chin | |
| 2015/0105828 A1 | 4/2015 | Reckling | |
| 2015/0112444 A1 | 4/2015 | Aksu | |
| 2015/0327872 A1 | 11/2015 | Assell | |
| 2016/0128838 A1 | 5/2016 | Assell | |
| 2017/0007409 A1 | 1/2017 | Mauldin | |
| 2017/0296346 A1 | 10/2017 | Assell | |
| 2018/0104071 A1 | 4/2018 | Reckling | |
| 2018/0318091 A1 | 11/2018 | Donner et al. | |
| 2018/0325675 A1 | 11/2018 | Donner | |
| 2018/0360608 A1 | 12/2018 | Aksu | |
| 2019/0083271 A1 | 3/2019 | Donner et al. | |
| 2019/0209011 A1 | 7/2019 | Donner et al. | |

OTHER PUBLICATIONS

Amendment Under 1.312, U.S. Appl. No. 15/993,170, dated Sep. 26, 2018.
Corrected Notice of Allowability, U.S. Appl. No. 15/828,622, dated Nov. 19, 2018.
Corrected Notice of Allowability, U.S. Appl. No. 15/993,170, dated Oct. 9, 2018.
Final Office Action, U.S. Appl. No. 14/660,784, dated Jul. 20, 2018.
Final Office Action, U.S. Appl. No. 15/418,633, dated Feb. 4, 2019.
Final Office Action, U.S. Appl. No. 15/729,273, dated Nov. 20, 2018.
Non-Final Office Action, U.S. Appl. No. 15/216,472, dated Sep. 25, 2018.

(56) References Cited

OTHER PUBLICATIONS

Non-Final Office Action, U.S. Appl. No. 15/385,446, dated Jul. 24, 2018.
Non-Final Office Action, U.S. Appl. No. 15/418,633, dated Aug. 7, 2018.
Non-Final Office Action, U.S. Appl. No. 15/662,045, dated Aug. 10, 2018.
Non-Final Office Action, U.S. Appl. No. 15/664,862, dated Oct. 3, 2018.
Non-Final Office Action, U.S. Appl. No. 15/785,997, dated Nov. 29, 2018.
Non-Final Office Action, U.S. Appl. No. 15/789,515, dated Oct. 29, 2018.
Non-Final Office Action, U.S. Appl. No. 15/789,602, dated Nov. 29, 2018.
Non-Final Office Action, U.S. Appl. No. 15/993,277, dated Nov. 26, 2018.
Notice of Allowance, U.S. Appl. No. 14/660,784, dated Nov. 15, 2018.
Notice of Allowance, U.S. Appl. No. 15/828,622, dated Aug. 9, 2018.
Notice of Allowance, U.S. Appl. No. 15/993,170, dated Aug. 8, 2018.
Notice of Allowance, U.S. Appl. No. 15/993,277, dated Dec. 4, 2018.
Preliminary Amendment, U.S. Appl. No. 15/831,589, dated Jul. 27, 2018.
Response to Final Office Action, U.S. Appl. No. 14/660,784, dated Oct. 22, 2018.
Response to Non-Final Office Action, U.S. Appl. No. 15/216,472, dated Dec. 19, 2018.
Response to Non-Final Office Action, U.S. Appl. No. 15/385,446, dated Oct. 24, 2018.
Response to Non-Final Office Action, U.S. Appl. No. 15/418,633, dated Nov. 7, 2018.
Response to Non-Final Office Action, U.S. Appl. No. 15/662,045, dated Nov. 12, 2018.
Response to Non-Final Office Action, U.S. Appl. No. 15/664,862, dated Jan. 2, 2019.
Response to Non-Final Office Action, U.S. Appl. No. 15/729,273, dated Aug. 1, 2018.
Response to Non-Final Office Action, U.S. Appl. No. 15/789,515, dated Nov. 21, 2018.
Response to Restriction, U.S. Appl. No. 15/664,608, dated Dec. 5, 2018.
Restriction Requirement, U.S. Appl. No. 15/664,608, dated Oct. 5, 2018.
Amendment Under 1.312, U.S. Appl. No. 15/993,277, dated Feb. 28, 2019.
Australian Examination Report, AU2017254857, dated Feb. 26, 2019.
Canadian Office Action, CA3002234, dated Jun. 13, 2019.
Final Office Action, U.S. Appl. No. 15/664,862, dated Apr. 24, 2019.
IN First Examination Report, 6569/DELNP/2012, dated Apr. 30, 2019.
Non-Final Office Action, U.S. Appl. No. 15/664,608, dated Apr. 1, 2019.
Non-Final Office Action, U.S. Appl. No. 15/729,273, dated Mar. 5, 2019.
Non-Final Office Action, U.S. Appl. No. 15/831,589, dated Jul. 1, 2019.
Notice of Allowance, U.S. Appl. No. 15/216,472, dated Mar. 20, 2019.
Notice of Allowance, U.S. Appl. No. 15/385,446, dated Feb. 21, 2019.
Notice of Allowance, U.S. Appl. No. 15/418,633, dated Jul. 25, 2019.
Notice of Allowance, U.S. Appl. No. 15/662,045, dated Mar. 26, 2019.
Notice of Allowance, U.S. Appl. No. 15/785,997, dated Jul. 3, 2019.
Notice of Allowance, U.S. Appl. No. 15/789,515, dated Mar. 27, 2019.
Notice of Allowance, U.S. Appl. No. 15/789,602, dated Jul. 2, 2019.
Response to Final Office Action, U.S. Appl. No. 15/418,633, dated May 2, 2019.
Response to Non-Final Office Action, U.S. Appl. No. 15/664,608, dated Jul. 1, 2019.
Response to Non-Final Office Action, U.S. Appl. No. 15/785,997, dated Feb. 28, 2019.
Response to Non-Final Office Action, U.S. Appl. No. 15/789,602, dated Mar. 25, 2019.

* cited by examiner

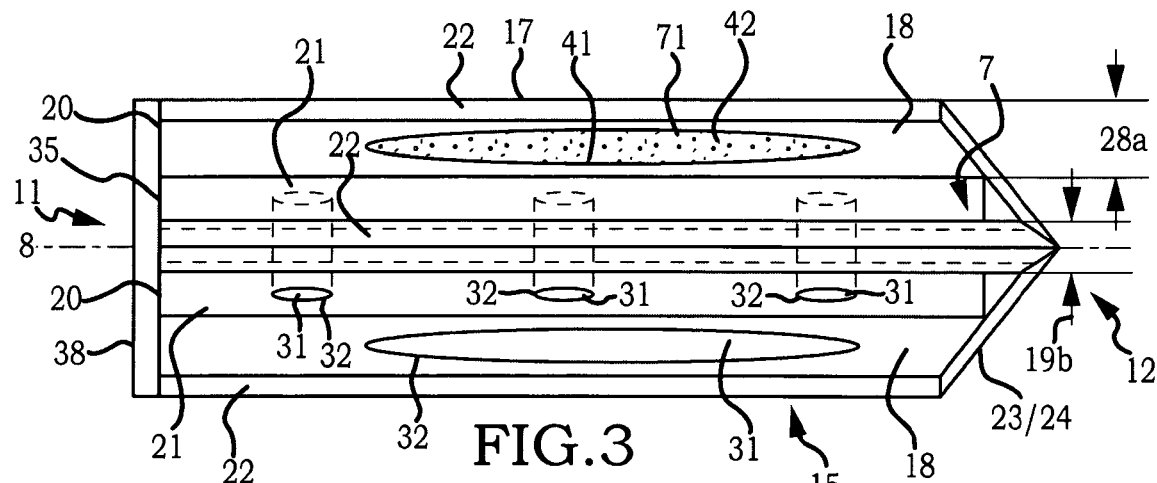
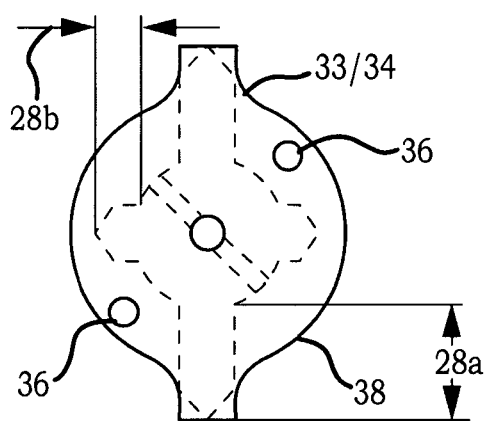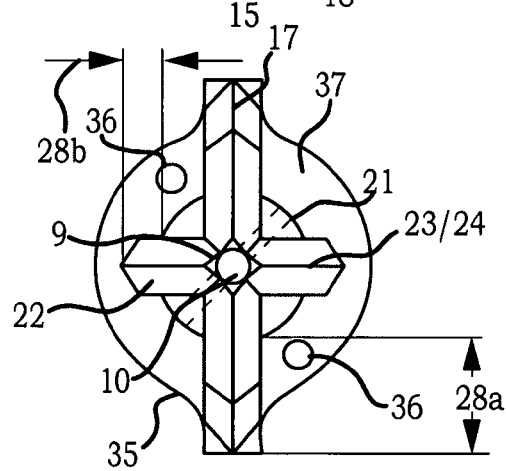
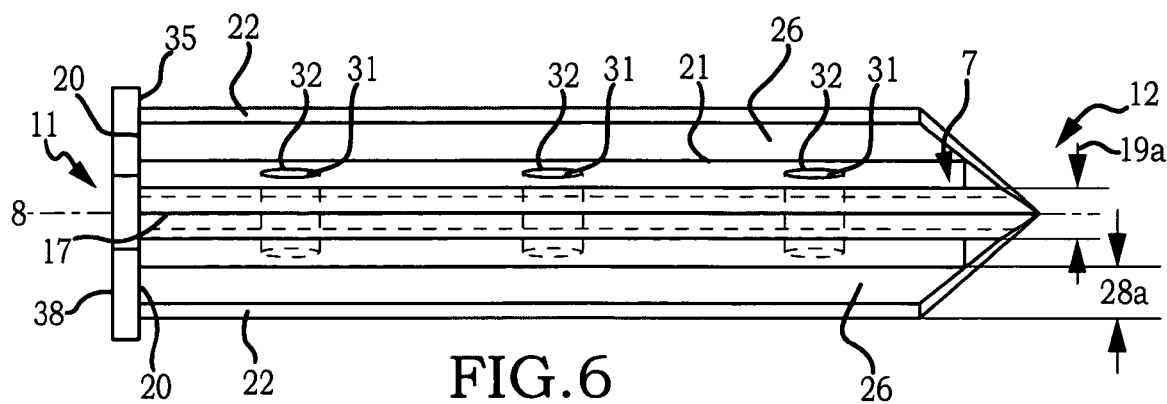

SINGLE IMPLANT SACROILIAC JOINT FUSION SYSTEM USING A POSTERIOR APPROACH FOR MINIMAL TISSUE DISRUPTION

CROSS REFERENCE TO RELATED APPLICATIONS

The present application is a continuation of U.S. patent application Ser. No. 15/992,987 filed May 30, 2018, which application is a continuation of U.S. patent application Ser. No. 15/910,753 filed Mar. 2, 2018, which application is a continuation of U.S. patent application Ser. No. 15/828,677 filed Dec. 1, 2017, now U.S. Pat. No. 9,931,212, which application is a continuation of U.S. patent application Ser. No. 15/061,524 filed Mar. 4, 2016, now U.S. Pat. No. 9,833,320, which application is a divisional of U.S. patent application Ser. No. 13/946,790 filed Jul. 19, 2013, now U.S. Pat. No. 9,333,090, which application claims priority to and incorporates by reference in its entirety U.S. Provisional Patent Application Nos. 61/674,277, filed Jul. 20, 2012; 61/800,120, filed Mar. 15, 2013; and 61/674,130, filed Jul. 20, 2012. Application Ser. No. 13/946,790 is also a continuation-in-part application of U.S. patent application Ser. No. 13/475,695 ("the '695 application"), which was filed May 18, 2012, now U.S. Pat. No. 9,381,045. The '695 application is a continuation-in-part application of and claims priority to U.S. patent application Ser. No. 13/236,411 ("the '411 application) filed Sep. 19, 2011, now U.S. Pat. No. 9,017,407.

The '411 application is a continuation-in-part application of and claims priority to U.S. patent application Ser. No. 12/998,712 ("the '712 application"), which was filed May 23, 2011, now U.S. Pat. No. 8,979,928. The '712 application is the National Stage of International Patent Cooperation Treaty Patent Application PCT/US2011/000070 (the "PCT application"), which was filed Jan. 13, 2011. The PCT application claims priority to U.S. Provisional Patent Application 61/335,947, which was filed Jan. 13, 2010.

The present application is also a continuation-in-part application of U.S. patent application Ser. No. 14/344,876, filed Mar. 13, 2014, which application is a National Stage of Patent Cooperation Treaty (PCT) Application No. PCT/US2012/055892, filed Sep. 18, 2012, which application is a continuation-in-part application of U.S. patent application Ser. No. 13/475,695 filed May 18, 2012, now U.S. Pat. No. 9,381,045, which application is a continuation-in-part application of U.S. patent application Ser. No. 13/236,411 ("the '411 application), filed Sep. 19, 2011, now U.S. Pat. No. 9,017,407.

The '411 application is a continuation-in-part application of and claims priority to U.S. patent application Ser. No. 12/998,712 ("the '712 application"), which was filed May 23, 2011, now U.S. Pat. No. 8,979,928. The '712 application is the National Stage of International Patent Cooperation Treaty Patent Application PCT/US2011/000070 (the "PCT application"), which was filed Jan. 13, 2011. The PCT application claims priority to U.S. Provisional Patent Application 61/335,947, which was filed Jan. 13, 2010.

All of the aforementioned applications are hereby incorporated by reference in their entireties into the present application.

The delivery approaches and methodologies disclosed in the above-listed applications and incorporated herein are applicable to the implants and delivery tools disclosed in the present application.

FIELD OF THE INVENTION

A sacroiliac joint fusion system that provides a method of fixation and fusion of the sacroiliac joint and sacroiliac fixation fusion implant which upon placement facilitates stability and fusion of the sacroiliac joint.

BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods encompassing an anterior approach, a posterior approach, and a lateral approach with or without percutaneous screw or other type implant fixation. However, while each of these methods have been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint including the anterior approach or posterior approach may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery. A danger to open surgery using the anterior approach can be damage to the L5 nerve root which lies approximately two centimeters medial to the sacroiliac joint. Additionally, these procedures typically involve fixation of the sacroiliac joint (immobilization of the articular surfaces of the sacroiliac joint in relation to one another) by placement of one or more screws or by placement of one or more trans-sacroiliac implants (as shown for example by the non-limiting example of FIG. 1) or by placement of implants into the S1 pedicle and iliac bone. Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to mal-placement of implants leading to damage of surrounding structures. Additionally, these procedures are often performed without fusion of the sacroiliac joint which does not remove the degenerative joint surface and thereby does not address the degenerative condition of the sacroiliac joint which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen which can be of relatively large dimension and which are subsequently broached with instruments which can result in bone being impacted into the pelvis and neuroforamen. The creation of the trans-sacroiliac bores and subsequent broaching of the bores requires a guide pin which may be inadvertently advanced into the pelvis or sacral foramen resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint which may result in continued or recurrent pain requiring additional surgery.

Another substantial problem with conventional procedures can be that placement of posterior intra-articular distracting fusion implants and bone grafts as described for example by U.S. patent application Ser. No. 10/797,481 of Stark, now U.S. Pat. No. 7,648,509, may be inadequate with respect to removal of the articular surface or cortical bone, the implant structure and fixation of the sacroiliac joint. The method may not remove sufficient amounts of the articular surfaces or cortical surfaces of the sacroiliac joint to relieve pain in the sacroiliac joint. The implant structures described may have insufficient engagement with the articular surfaces or cortical bone of the sacroiliac joint for adequate fixation or fusion. The failure to sufficiently stabilize and fuse the sacroiliac joint with the implant structures and methods described by the Stark application may result in a failure to relieve the condition of sacroiliac joint being treated.

The inventive sacroiliac fusion system described herein addresses the problems associated with conventional methods and apparatuses used in fixation and fusion of the sacroiliac joint.

SUMMARY OF THE INVENTION

Accordingly, a broad object of the invention can be to provide an inventive fixation fusion implant for fixation and fusion of the sacroiliac joint. Embodiments of the fixation fusion implant can provide a first pair of radial members which extend in generally opposed relation a distance radially outward from the longitudinal axis of a generally linear elongate body and as to certain embodiments can further provide a second pair of radial members which extend in generally opposed relation a distance radially outward from the longitudinal axis of the generally linear elongate body and can be in substantially perpendicular relation to the first pair of radial members.

Another broad object of the invention can be to provide an inventive method for fixation and fusion of the sacroiliac joint which utilizes the inventive fixation fusion implant. The inventive method comprises the steps of performing a minimally invasive posterior surgery that allows access to the posterior lateral aspect of the sacroiliac joint for removing a sufficient portion of the cartilage and subchondral bone to relieve the condition for which the sacroiliac joint is being treated and to configure a portion of the sacroiliac joint to provide an implant receiving space in the plane of the sacroiliac joint (non-trans-sacroiliac) configured to allow interference fitting of the first pair radial members of the fixation fusion implant between the opposed surfaces of the implant receiving space, and thereby locating the first one of the second pair of radial members in the bone of the sacrum and the second one of the second pair of radial members in the bone of the ilium. The inventive method avoids conventional trans-sacroiliac placement of S1 pedicle or intrailiac screws while providing immediate fixation of the sacroiliac joint.

Another broad object of the invention can be to provide one or more bone ingrowth aperture elements which communicate between the opposed surfaces of the first pair of radial members or through the generally linear elongate body each having a configuration which allows the bone of the sacrum and ilium to grow through the implant to facilitate fusion of the sacrum to the ilium and fixation of the sacroiliac joint.

Another broad object of the invention can be to provide particular embodiments of the inventive fixation fusion implant with an amount of curvature along the length of the implant which allows placement of embodiments of the fixation fusion implant which have an increased surface area which remain within the articular portion of the sacroiliac joint.

Naturally, further objects of the invention are disclosed throughout other areas of the specification, drawings, photographs, and claims.

BRIEF DESCRIPTION OF THE DRAWINGS

FIG. 3 is a first side view of a particular embodiment of the fixation fusion implant.

FIG. 4 is a first implant end view of a particular embodiment of the fixation fusion implant.

FIG. 5 is a second implant end view of a particular embodiment of the fixation fusion implant.

FIG. 6 is second side view of the particular embodiment of the fixation fusion implant shown in FIG. 3 rotated about 90 degrees about the longitudinal axis.

DETAILED DESCRIPTION OF THE PREFERRED EMBODIMENTS

Generally, a sacroiliac joint fusion system that provides a method of fixation and fusion of the sacroiliac joint and a fixation fusion implant which upon placement within the sacroiliac joint facilitates stability and fusion of the sacroiliac joint.

Figure 1:
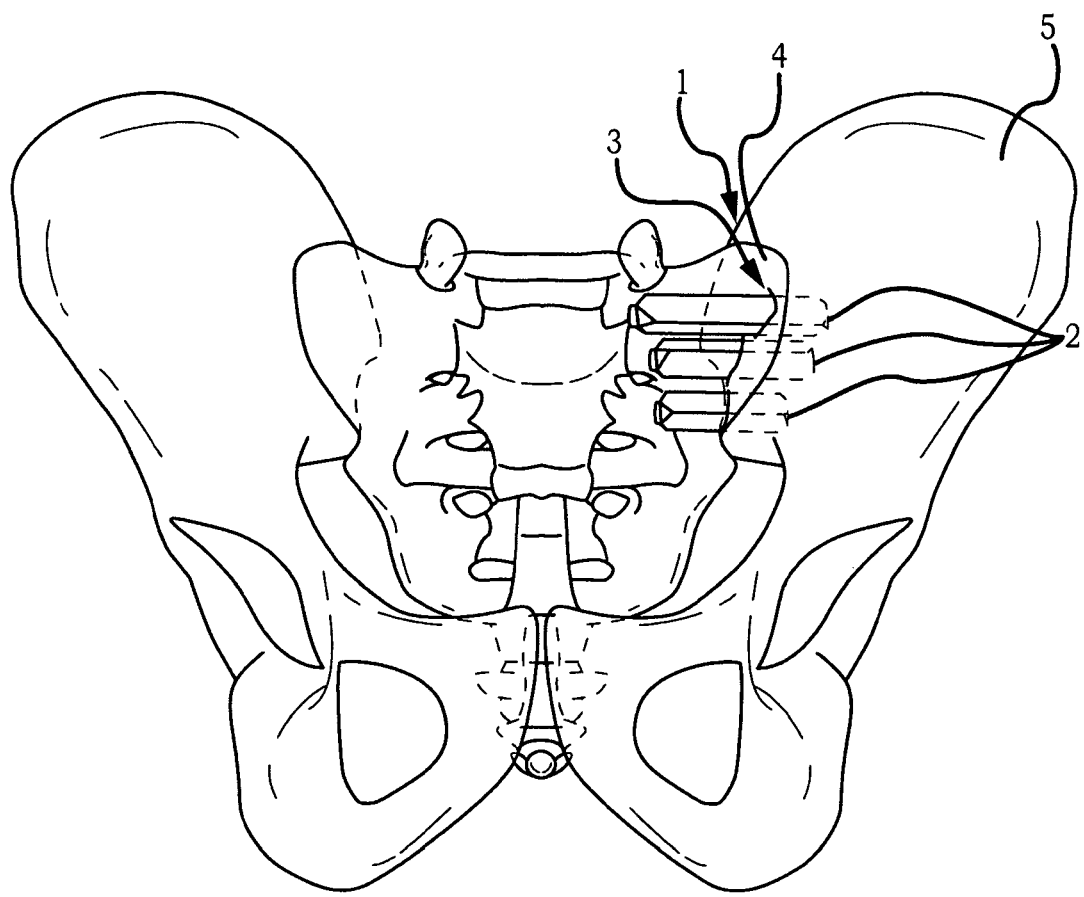
FIG. 1 is an anterior view of the pelvic region and a conventional method and device for stabilizing the sacroiliac joint.

Now referring primarily to FIG. 1, which shows one commonly utilized conventional method and device for fixation of the sacroiliac joint (1). The conventional device shown comprises one or more substantially linear elongate members (2) which can be inserted into correspondingly dimensioned trans-iliac bores (3) with a first portion extending in the bone of sacrum (4) and a second portion extending into the bone of the ilium (5) thereby extending cross the sacroiliac joint (1). The one or more substantially linear elongate members (2) (which can be configured as cylindrical rods which can further include an amount of taper or further include a spiral thread coupled to the exterior surface to avoid the need for generating trans-iliac bores) in trans-iliac placement can locate the ilium (5) in fixed relation to the sacrum (4). However, this trans-iliac placement of such substantially linear elongate members (2) can have the disadvantages above described.

Figure 2:
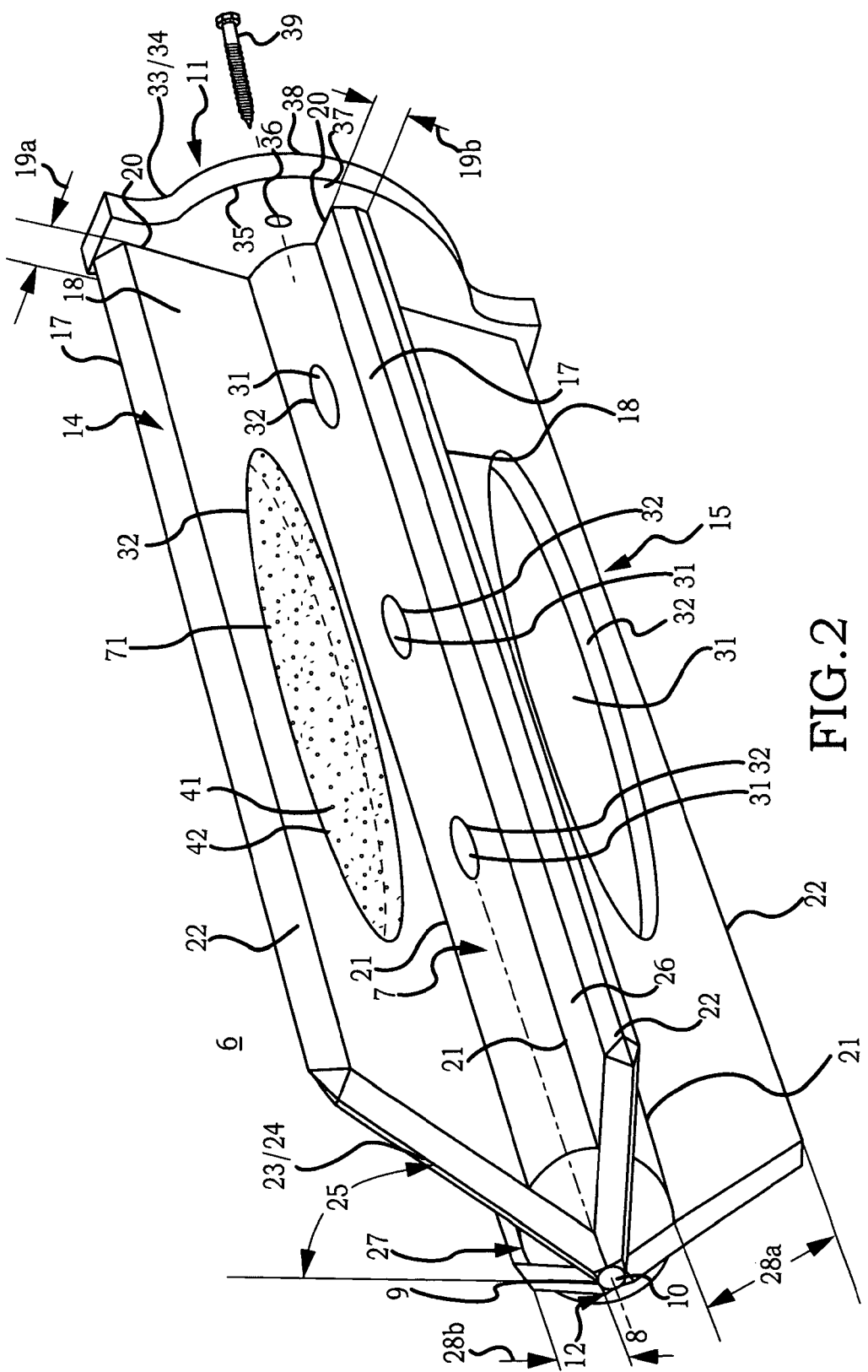
FIG. 2 is a perspective view of a particular embodiment of the fixation fusion implant.

Now referring primarily to FIG. 2 and also FIGS. 3-6, an embodiment of an inventive fixation fusion implant (6) is shown which in part includes an elongate body (7) which defines a longitudinal axis (8). The elongate body (7) has a configuration of sufficient dimension to avoid deformation under the normal forces of surgical placement and fixation of the ilium (5) in relation to the sacrum (4). Accordingly, while the embodiment of the fixation fusion implant (6) shown in FIG. 2 can be generally cylindrical or circular in cross section; the invention is not so limited, and the elongate body (7) can have any of a numerous and varied configurations consistent with the method herein after described such as oval, triangular, rectangular, square, diamond, or the like. As one non-limiting example, the generally cylindrical elongate body (7) shown in FIG. 2 can depending on the application have a diameter of in the range of about 0.5 centimeters ("cm") to about 1 cm and a length disposed between a first end and a second end in the range of about 3 cm and about 6 cm.

As to particular embodiments of the invention, the elongate body (7) can further include an axial bore (9) that bounds an axial pathway (10) which communicates between a first implant end (11) and a second implant end (12) of the elongate body (7). The axial bore (9) allows for placement within the axial pathway (10) a guide wire (13) (or other guide member) on which embodiments of the fixation fusion implant (6) can be guided for insertion into the sacroiliac joint (1)(further described below).

Again referring primarily to FIG. 2 and FIGS. 3-6, embodiments of the fixation fusion implant (6) can further include a first radial member (14) and a second radial member (15) each coupled to the external surface of the elongate body (7) generally in line with the longitudinal axis (8) and substantially the entire length of the elongate body (7). Each of the first radial member (14) and the second radial member (15) can extend radially outward from the elongate body (7) substantially in opposed relation (180 degrees apart about the elongate body (7)); however, the invention is not so limited, and as to certain embodiments, the first radial member (14) and the second radial member (15) can be spaced about the elongate body (7) a greater or lesser number of degrees. While the configuration of each of the first radial member (14) or second radial member (15) can vary as necessary to provide a correspondingly variable amount of surface area engageable within the plane of the articular surfaces (16) of the sacrum (4) and ilium (5) sufficient for fixation of the sacroiliac joint (1) upon implantation, each the first radial member (14) and the second radial member (15)(and additional radial members) can each include a pair of opposed faces (17)(18) disposed a thickness (19a) apart and having an area bound by a top edge (20), a pair of side edges (21)(22) and a bottom edge (23). The first of the pair of side edges (21) can be connected as above described to the elongate body (7) locating the second side edge (22) a distance outward from the longitudinal axis (8) of the elongate body (7). As a non-limiting example, each of the first radial member (14) and the second radial member (15) can be substantially rectangular in configuration having a height (28a) between the first of the pair of side edges (21) and the second of the pair of side edges (22) in the range of about 0.2 cm and about 1 cm. Understandably, a lesser diameter elongate body (7) may include a first radial member (14) and a second radial member (15)(or other radial members) having greater height (28a) and a greater diameter elongate body (7) may require a first radial member (14) and a second radial member (15)(or other radial members) having lesser height (28a).

The top edge (20) of each of the first radial member (14) and the second radial member (15) can terminate substantially in alignment with the first implant end (11) of the elongate body (7). The bottom edge (23) of the first radial member (14) and the second radial member (15) can terminate substantially in alignment with second implant end (12) of the elongate body (7). As to certain embodiments, the bottom edge (23) can further include an angle element (24) which angles outward from the elongate body (7) commencing at the second implant end (12) and joining the second of pair of side edges (22) a distance toward the first implant end (11). The angle element (24) can have a degree angle (25) from perpendicular with the longitudinal axis (8) in a range of about fifteen degrees to about thirty degrees, as shown in FIG. 2.

Again referring primarily to FIG. 2 and FIGS. 3-6, certain embodiments of the fixation fusion implant (6) can further include a third radial member (26) and as to certain embodiments a fourth radial member (27) each coupled to the external surface of the elongate body (7) at a location which allows upon implantation at least a portion of the third radial member (26) to locate in the bone of the sacrum (4) or the ilium (5) and the fourth radial member (27) to locate in the bone of the sacrum (4) or the ilium (5). As to the non-limiting embodiment of the fixation fusion implant (6) shown in FIG. 3, the third radial member (26) and the fourth radial member (27) can be connected generally in line with the longitudinal axis (8) of the elongate body (7). Each of the third radial member (26) and the fourth radial member (27) can extend radially outward from the elongate body (7) substantially in opposed relation (about 180 degrees apart) and in perpendicular relation (about 90 degrees) to the first radial member (14) and the second radial member (15)(see also FIGS. 8 and 9; however, the invention is not so limited, and the third radial member (26) and the fourth radial member (27)(if the embodiment includes a fourth radial member (27)) can be spaced about the elongate body (7) in relation to each other and in relation to the first radial member (14) and the second radial member (15) a greater or lesser number of degrees depending on the application and the amount of desired engagement with the bone of the sacrum (4) or ilium (5).

The configuration of each of the third radial member (26) or the fourth radial member (27) can vary as necessary to provide an amount of surface area engageable with the bone of the sacrum (4) and ilium (5) sufficient for facilitating fixation of the sacroiliac joint (1) upon implantation and to further provide a resistance to rotation or other undesired movement of the fixation fusion implant (6) at the implant location in the sacroiliac joint (1). Accordingly, embodiments of the fixation fusion implant (6) having a third radial member (26) and the fourth radial member (27) can provide a pair of opposed faces (17)(18) disposed a thickness (19b) apart and have an area bound by a top edge (20), a pair of side edges (21) (22) and a bottom edge (23) in similar configuration as above described for the first radial member (14) and the second radial member (15). The first of the pair of side edges (21) can be connected as above described to the elongate body (7) locating the second side edge (22) a distance outward from the longitudinal axis (8) of the elongate body (7). As a non-limiting example, each of the third radial member (26) and the fourth radial member (27) can have a substantially rectangular configuration having a height (28b) between the first of the pair of side edges (21) and the second of the pair of side edges (22) in the range of about 0.1 cm and about 0.4 cm. The top edge (20) of each of the third radial member (26) and the fourth radial member (27) can terminate substantially in alignment with the first implant end (11) of the elongate body (7). The bottom edge (23) of the third radial member (26) and the fourth radial member (27) can terminate substantially in alignment with second implant end (12) of the elongate body (7). As to certain embodiments, the bottom edge (23) of the third radial member (26) and the fourth radial member (27) can further include the angle element (24) which angles the second of the pair of side edges (22) toward the first implant end (11) of the elongate body (7). The angle element (24) can have a degree angle (25) from perpendicular with the longitudinal axis (8) in a range of about fifteen degrees to about thirty degrees; however, the invention is not so limited and with respect to certain embodiments of the invention there may be no angle element (24) or the angle element may be greater or less than within the range of about fifteen degrees to about thirty degrees. Additionally, the angle element (24) can be similar as shown in the figures or can be dissimilar between the radial members of a particular fixation fusion implant (6) depending on the application.

Again referring primarily to FIG. 2 and FIGS. 3-6, and without limitation to forgoing, the third radial member (26) and the fourth radial member (27) can have a lesser height (28b) than the first radial member (14) and second radial member (15) because while the structure of the third radial member (26) and the fourth radial member (27) appear similar to the first radial member (14) and the second radial member (15), the function is substantially different. The first radial member (14) and the second radial member (15) have a configuration (height, length, thickness, surface area, and location on the external surface of the elongate body, as above described) capable of or allowing interference fit within an implant receiving space (29) surgically produced in the articular plane (30) of the sacroiliac joint (1), as further described below, and capable of fixation of the sacroiliac joint (1) upon placement within the implant receiving space (29), and which can further allow for incorporation by bony ingrowth about and through the fixation fusion implant (6) or osseointegration with the external surface of the fixation fusion implant (6)(or both) resulting in fusion of the sacroiliac joint (1). By contrast, the third radial member (26) and as to those embodiments having a fourth radial member (27) have a configuration (height, length, thickness, surface area, and location on the external surface of the elongate body, as above described) capable of being forcibly urged a depth into the cancellous bone of the sacrum (75) or cancellous bone of the ilium (76) as the implant receiving space (29) receives the fixation fusion implant (6) to an extent sufficient to further resist rotation of the fixation fusion implant (6) subsequent to placement in the implant receiving space (29) and boney fusion of the cancellous bone to the fixation fusion implant (6).

Again referring primarily to FIG. 2 and FIGS. 3-6, particular embodiments of the fixation fusion implant (6) can further include one or more aperture elements (31) which communicate between the opposed faces (17)(18) of the first radial member (14) or the second radial member (15) or both. The amount of open space of an aperture element (31) can be defined by an aperture perimeter (32) which can be of numerous and varied configurations of sufficient dimension to allow the surfaces of the ilium (5) or sacrum (4)(or both) adjacent to the first radial member (14) or the second radial member (15)(or both) of the fixation fusion implant (6) placed within the implant receiving space (29) to grow a distance into the aperture element (31) or through the aperture element (31) or fuse within the aperture element (31). As a non-limiting example, the aperture perimeter (32) can be of generally oval configuration resulting in an oval aperture element (31) located in the first radial member (14) or the second radial member (15)(or both)(or located in additional radial members depending upon the embodiment) with the length of the oval aperture element (31) aligned with the length of the first radial member (14) or second radial member (15) and being about one quarter to about two thirds the length of the radial member and having a width of the oval aperture element (31) located between the sides (21)(22) of the first radial member (14) or second radial member (15) and being about one quarter to about two thirds the height (28a). Additionally, the elongate body (7) can further include aperture elements (31) which communicate between the external surfaces between the radial members (14)(15)(26)(27).

Again referring primarily to FIG. 2 and FIGS. 3-6, embodiments of the fixation fusion implant (6) can further include an anti-migration element (33) coupled to the first implant end (11) of the elongate body (7). The anti-migration element (33) can take the form of an enlarged terminal portion of the first end of the elongate body (7), an increase in the height (28) of one or more of the radial members (such as flaring outward) proximate the first implant end (11) of the elongate body (7). As one non-limiting example, the anti-migration element (33) can take the form of an end cap (34) having a generally circular configuration with the center substantially aligned with the longitudinal axis (8) of the elongate member 0 and extending radially outward sufficient distance to prevent advancement of the second implant end (12) of the fixation fusion implant (6) further into the sacroiliac joint (1) subsequent to implantation in the implant receiving space (29). While the end cap (34) shown is generally circular in configuration, the end cap (34) can have end cap perimeter (35) which defines an oval, square, rectangle, or other configuration useful in fixing the location of the fixation fusion implant (6) in relation the sacroiliac joint (1). Additionally, the anti-migration element (33) can have sufficient dimensions to further include one or more bores (36) which communicate between the opposed surfaces (37)(38) of the anti-migration element (33) and dimensioned to receive mechanical fasteners (39)(such threaded members, barbed members, locking members or the like) which can be driven or rotated to engage a portion of the mechanical fastener with the sacrum (4) or the ilium (5).

The elongate body (7) along with the other elements of the fixation fusion implant (6) above described can be fabricated or formed from a plurality of pieces or as a single piece of biocompatible material or a combination of biocompatible and biodegradable materials of suitably dimensioned particles, sheets, or other constructional forms or formable or moldable materials suitably bound or formed or molded to provide configurations in accordance with the invention.

Figure 7:
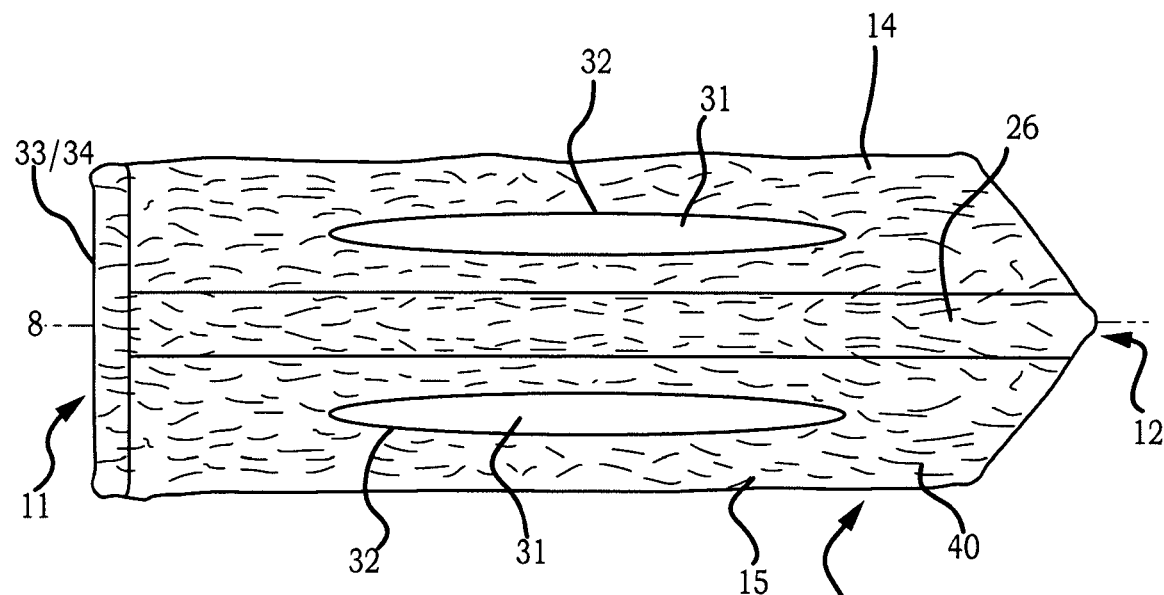
FIG. 7 is a first side view of another particular embodiment of the fixation fusion implant having a coat material which facilitates osseointegration of the fixation fusion implant with the bone.
Figure 8:
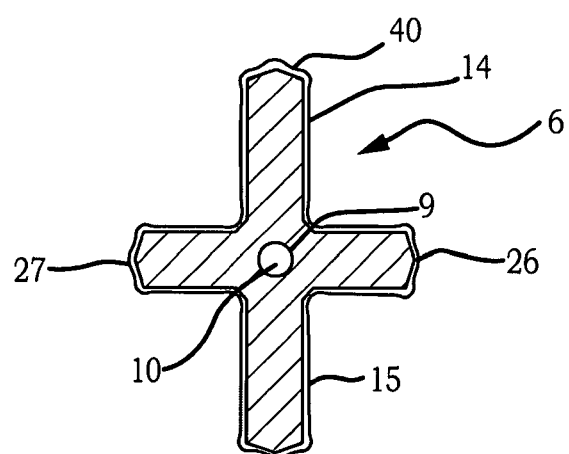
FIG. 8 is a cross section 8-8 as shown in FIG. 7 of that particular embodiment of the fixation fusion implant.
Figure 9:
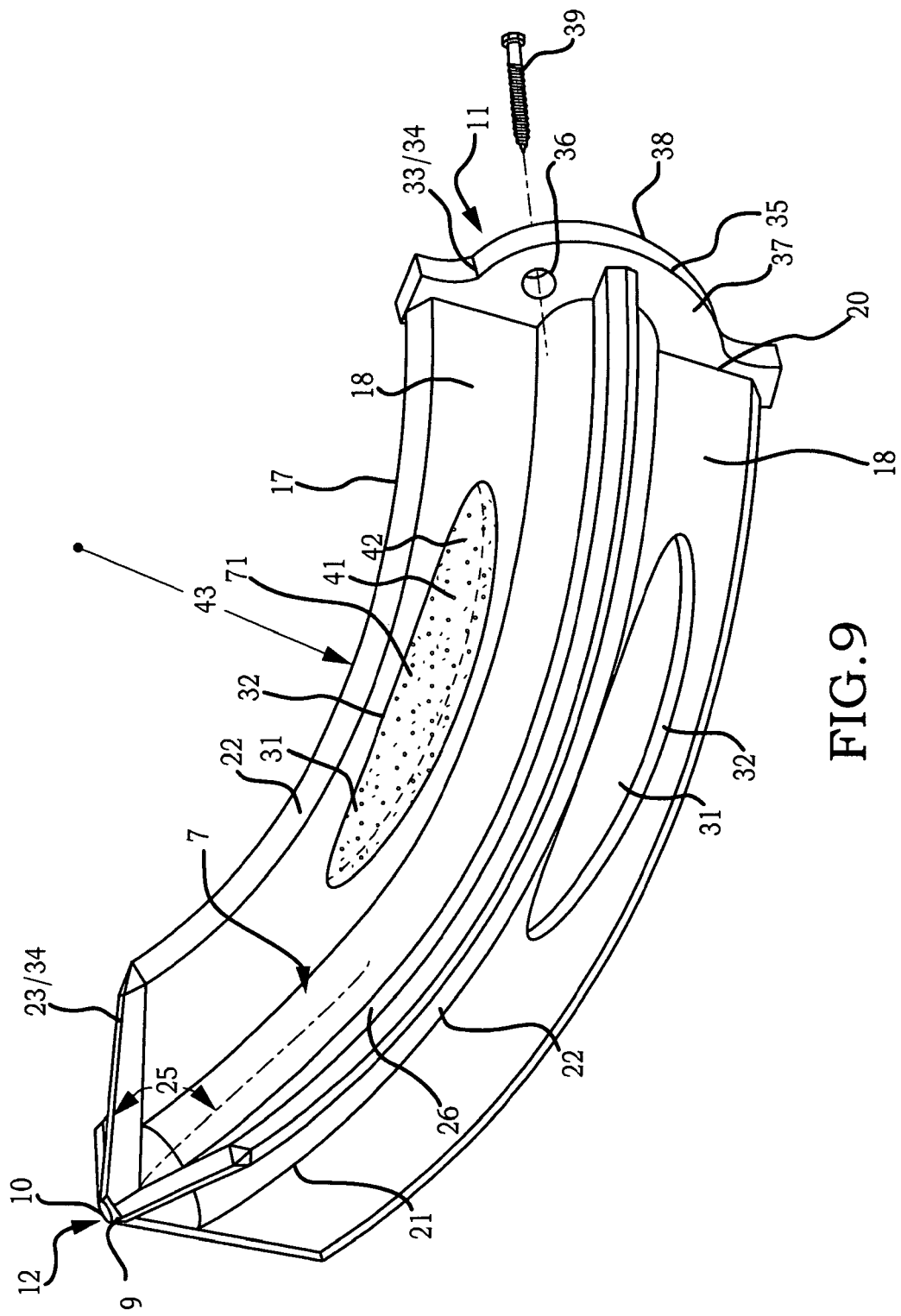
FIG. 9 is a perspective view of an embodiment of the fixation fusion implant having an amount of curvature along the longitudinal axis.
Figure 10:
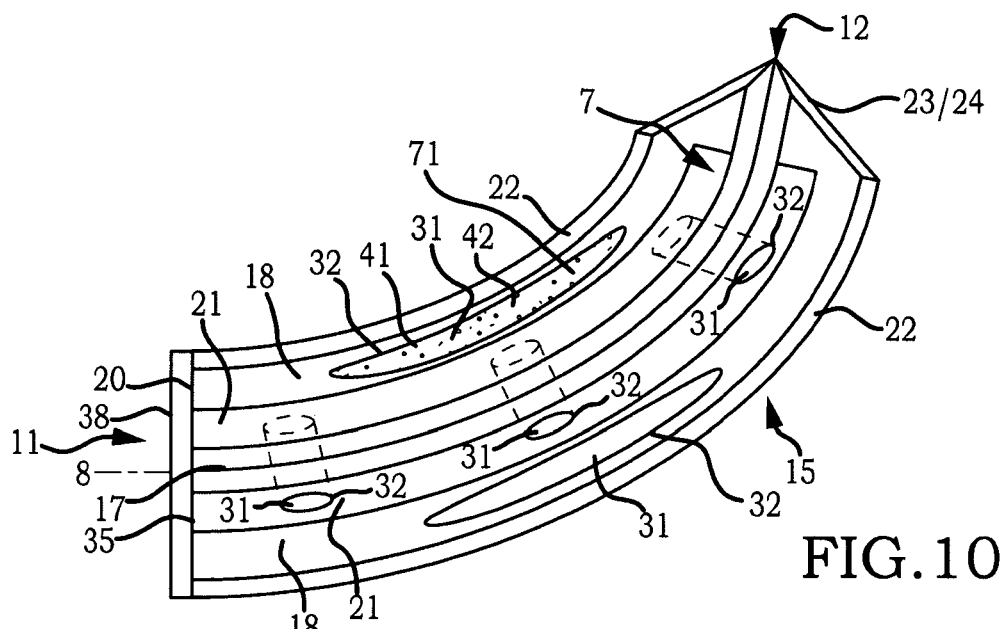
FIG. 10 is a first side view of the particular embodiment of the fixation fusion implant shown in FIG. 9.
Figure 11:
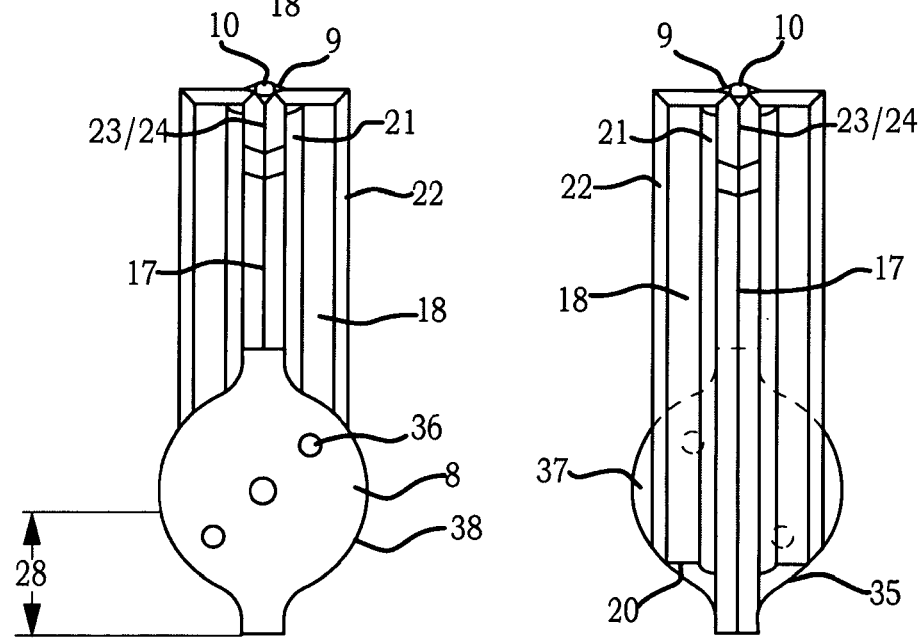
FIG. 11 is a first implant end view of a particular embodiment of the fixation fusion implant shown in FIG. 9.
Figure 12:
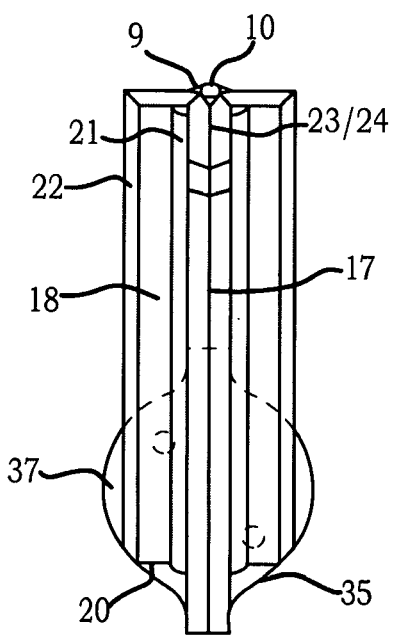
FIG. 12 is a second implant end view of a particular embodiment of the fixation fusion implant shown in FIG. 9.
Figure 13:
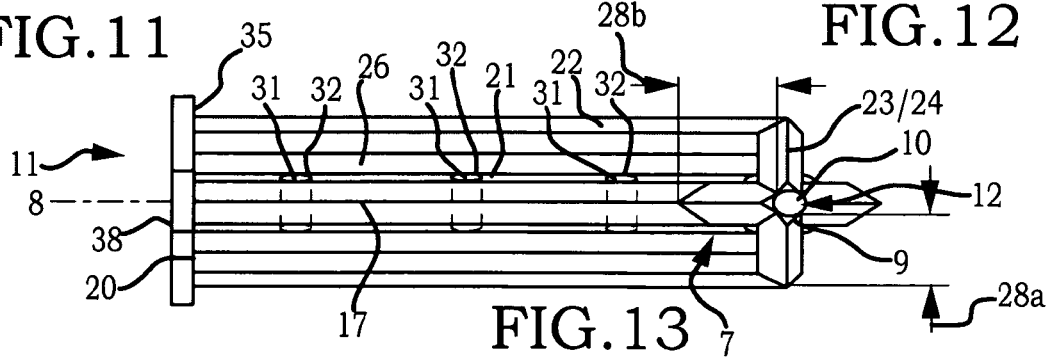
FIG. 13 is second side view of the particular embodiment of the fixation fusion implant shown in FIG. 10 rotated about 90 degrees about the longitudinal axis.

Now referring primarily to FIGS. 7 and 8, embodiments of the fixation fusion implant (6) can further include a coat (40) coupled to or generated on all or a part of the external surface of the fixation fusion implant (6). The coat (40) can be of any composition that can be coupled to the fixation fusion implant (6) capable of biocompatible osseointegration with the bone of the ilium (5) and sacrum (4), such as pure alumina, titanium-dioxide, hydroxyapatite, calcium triphosphate, or the like. As a non-limiting example, the coat (40) can be applied by plasma spraying with a plasma torch, plasmatron or a plasma gun. Alternately, the coat (40) can be achieved by producing a surface roughness, porosity, or irregularity of the fixation fusion implant (6) by sand blasting, bead blasting, molding, or the like. The coat (40) can have a thickness in the range of about 40 gm and about 100 gm. Again, embodiments of the fixation fusion implant (6) can be configured as a material having interconnecting pores throughout such as TRABECULAR METAL available from Zimmer, P.O. Box 708, 1800 West Center Street, Warsaw, Ind. 46581-0708 or a metallic foam such as a titanium foam available from the National Research Council Canada, 1200 Montreal Road, Bldg. M-58, Ottawa, Ontario, Canada.

Again referring primarily to FIG. 2 and FIGS. 3-6, embodiments of the invention can further include one or more biologically active agent(s) (41) which can be applied directly to the external surface of the fixation fusion implant (6) or can be mixed with a biocompatible material or biocompatible biodegradable material which can be applied to the external surface of the fixation fusion implant (6) or otherwise made a part of the fixation fusion implant (6). As to particular embodiments of the fixation fusion implant (6), the biologically active agent(s)(41) can be mixed with an amount of a biocompatible biodegradable material (71) and located within one or more of the aperture elements (31).

"Biocompatible" for the purposes of this invention means the ability of any material to perform the intended function of an embodiment of the invention without eliciting any undesirable local or systemic effects on the recipient and can include non-biodegradable materials such as: ceramic; metals or steels such as titanium alloys or rigid polymeric materials or rigid laminate materials or composites which include suitably dimensioned particles of metals or steels dispersed within rigid laminate materials, or suitably sized particles of biocompatible materials suitably bound or formed to provide configurations, polyurethanes, polyisobutylene, ethylene-alpha-olefin copolymers, acrylic polymers and copolymers, vinyl halide polymers and copolymers, polyvinyl esters, polyvinylidene chloride, polyacrylonitrile, polyvinyl ketones, polyvinyl aromatics such as polystyrene, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyesters, epoxy resins, rayon-triacetate, cellophane, polyether ether ketone (PEEK), bone-from-wood available from the Istituto di Scienza e Tecnologia dei Mareriali Ceramici, Faenza, Italy, or the like, or biodegradable materials, as herein described.

"Biodegradable" for the purposes of this invention means the ability of any biocompatible material to breakdown within the physiological environment of the sacroiliac joint by one or more physical, chemical, or cellular processes at a rate consistent with providing treatment of a condition of the sacroiliac joint at a therapeutic level controllable by selection of a polymer or mixture of polymers (also referred to as polymeric materials), including, but not limited to: polylactide polymers (PLA), copolymers of lactic and glycolic acids (PLGA), polylactic acid-polyethylene oxide copolymers, poly(ε-caprolactone-co-L-lactic acid (PCL-LA), glycine/PLA copolymers, PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly(phosphoesters) by matrix or pendant delivery systems, poly (phosphazenes), poly(iminocarbonate), crosslinked poly(ortho ester), hydroxylated polyester-urethanes, or the like.

"Biologically active agents" for the purposes of this invention means those agents or mixture of agents which can be varied in kind or amount to provide a therapeutic level effective to mediate the formation or healing of bone, cartilage, tendon, or to reduce, inhibit, or prevent a symptom of a condition of the sacroiliac joint subsequent to placement of an embodiment of the fixation fusion implant within the sacroiliac joint (1) such as infection or pain and without limitation can include agents that influence the growth of bone, alleografts, bone forming protein, bone morphogenetic protein 2, analgesics, anesthetics, anti-inflammatory agents, antibacterials, antivirals, antifungals, antiprotozoals, anti-infectives, antibiotics such as aminoglycosides such as gentamicin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline, minocycline, and doxycycline; quinolones such as ciprofloxacin, moxifloxacin, gatifloxacin, and levofloxacin; anti-viral drugs such as acyclovir, gancyclovir, vidarabine, azidothymidine, dideoxyinosine, dideoxycytosine; analgesics, such as codeine, morphine, ketorolac, naproxen, an anesthetic, lidocaine; cannabinoids; antifungal agents such as amphotericin; anti-angiogenesis compounds such as anecortave acetate; retinoids such as tazarotene, steroidal anti-inflammatory agents such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide; and any of their derivatives.

As to particular embodiments of the inventive fixation fusion implant (6) the biologically active agent(s)(41) can be dispersed throughout a biocompatible or biocompatible biodegradable material (or mixture of biocompatible materials or mixture of biocompatible biodegradable materials) by mixing biologically active agent(s)(41) into the melted biocompatible or biodegradable polymer and then solidifying the resulting material by cooling, having the biologically active agent(s)(41) substantially uniformly dispersed throughout. The biodegradable material or biocompatible material or mixture thereof can be selected to have a melting point that is below the temperature at which the biologically active agent(s)(41) becomes reactive or degrades. Alternatively, the biologically active agent(s)(41) can be dispersed throughout the biocompatible or biodegradable material by solvent casting, in which the biocompatible or biodegradable material is dissolved in a solvent, and the biologically active agent(s)(41) dissolved or dispersed in the solution. The solvent is then evaporated, leaving the biologically active agent(s)(41) in the matrix of the biocompatible or biodegradable material. Solvent casting requires that the biocompatible or biodegradable material be soluble in organic solvents. Alternatively, the fixation fusion implant (6) can be placed in a solvent having a concentration of the biologically active agent(s)(41) dissolved and in which the fixation fusion implant (6) or the biocompatible or biocompatible biodegradable material located in the aperture elements, or applied to the external surface, swells. Swelling of the fixation fusion implant (6) or portions thereof draws in an amount of the biologically active agent(s) (41). The solvent can then be evaporated leaving the biologically active agent(s)(41) within the biocompatible or biocompatible biodegradable material. As to each method of dispersing the biologically active agent(s) (41) throughout the biocompatible or biodegradable biocompatible material of or coupled to the fixation fusion implant (6), therapeutic levels of biologically active agent(s) (41) can be included in biocompatible biodegradable material to provide therapeutically effective levels of the biologically active agent to the sacroiliac joint (1) to treat a particular sacroiliac joint condition.

Other non-active agents (42) may be included in the biocompatible biodegradable material for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA or other appropriate agencies in the United States or foreign countries, for the desired route of administration. Electrolytes such as sodium chloride and potassium chloride may also be included in the formulation.

A non-limiting example, embodiments of the fixation fusion implant (6) having a biocompatible biodegradable portion with biologically active agent(s)(41) for treating the sacroiliac joint (1) can be made by dispersing a biologically active agent(s)(41) in a biocompatible biodegradable material as above described to provide biologically active agent (s) (41) release characteristics at a therapeutic level. Upon implantation of the fixation fusion implant (6) in the sacroiliac joint (1) as described below, the biocompatible biodegradable portion of the fixation fusion implant (6) can substantially continuously release biologically active agent (41) to provide a localized amount of bone morphogenetic protein 2 at therapeutic levels of about 1 milligram to about 4 milligrams to facilitate bone regrowth. It is to be understood that this specific example of providing an embodiment of the fixation fusion implant (6) which delivers an amount of bone morphogenetic protein 2 to facilitate bone regrowth, is not intended to be limiting, and embodiments of the fixation fusion implant (6) can be utilized to deliver numerous and varied active agent(s)(41) individually or in combination to treat a wide range of conditions of the sacroiliac joint (1) subsequent to implantation of embodiments of the fixation fusion implant (6).

Now referring primarily to FIGS. 9-13 and 25, particular embodiments of the invention can further include an amount of curvature (43) between the first implant end (11) and the second implant end (12) of the fixation fusion implant (6). The amount of curvature (43) can vary from embodiment to embodiment of the fixation fusion implant (6) depending on the application between a substantially linear elongate body (7) as above described to including an amount of curvature (43) which defines a radius within a range of about 2 cm and about 6 cm.

Figure 25:
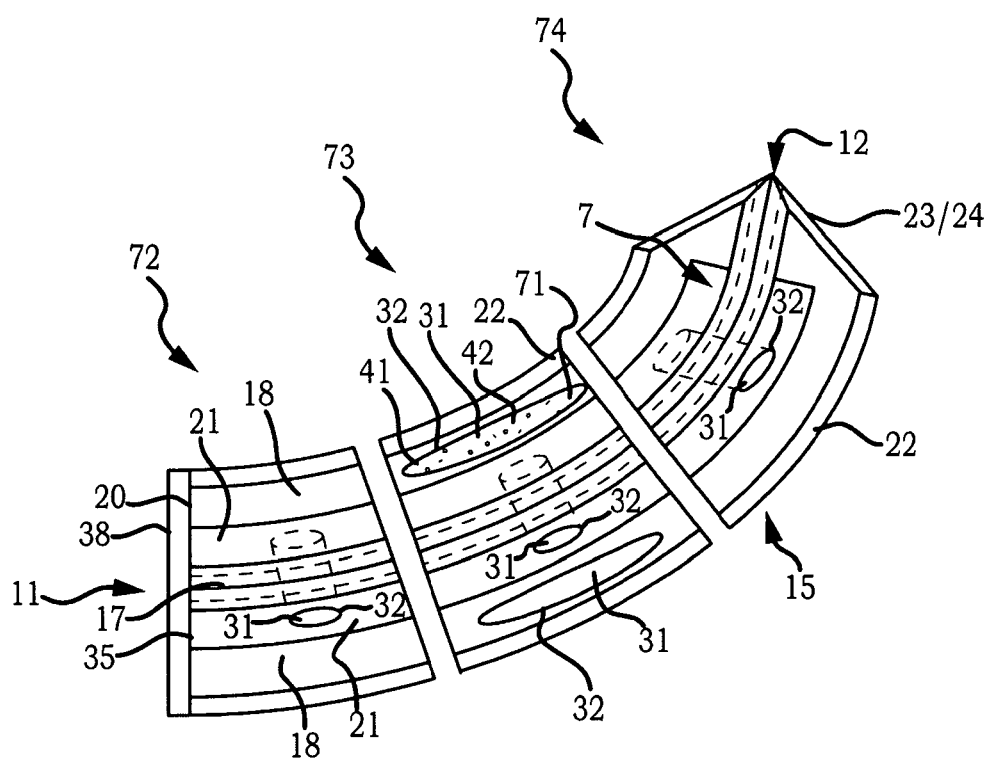
FIG. 25 is a perspective view of a particular embodiment of the fixation fusion implant having an amount of curvature along the longitudinal axis and further broken into implantable segments.
Figure 26:
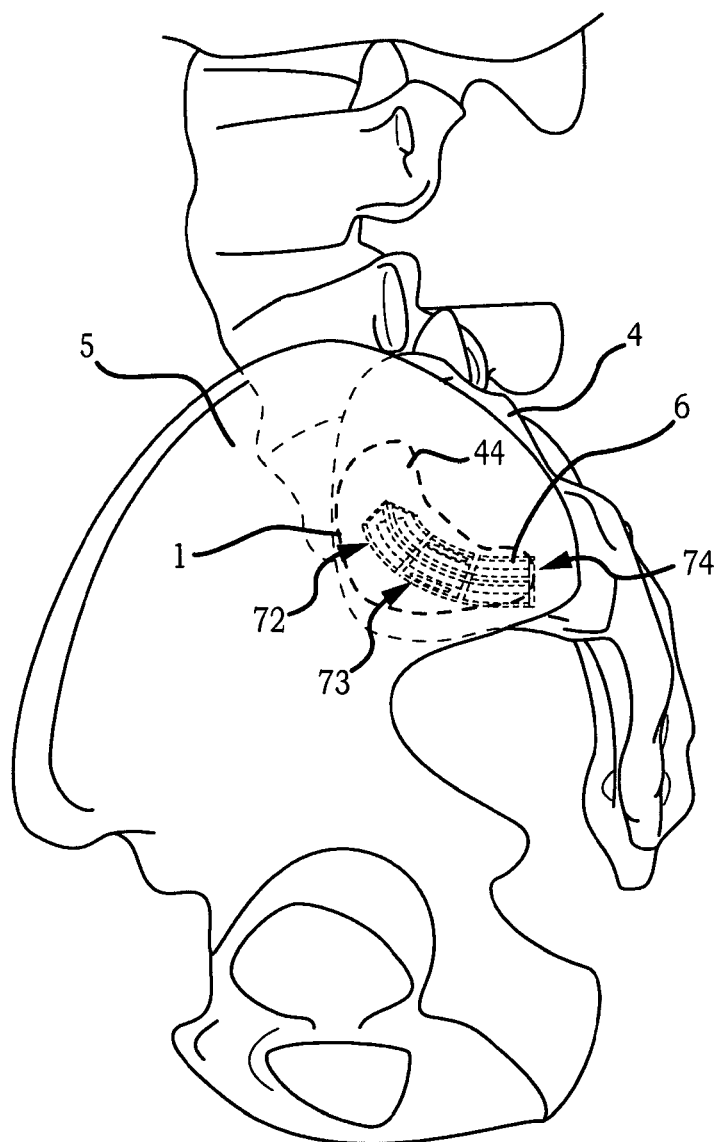
FIG. 26 provides a side view of the ilium with the articular surfaces of the sacroiliac joint and the embodiment of the fixation fusion implant shown in FIG. 25 located within the articular plane of the sacroiliac joint shown in broken line.

Now referring primarily to FIG. 25, certain embodiments of the invention having an amount of curvature can be provided in a plurality of implant segments (72)(73)(74) which can be individually implanted within the articular plane (44) as shown in FIG. 26 by the method below described.

Figure 22:
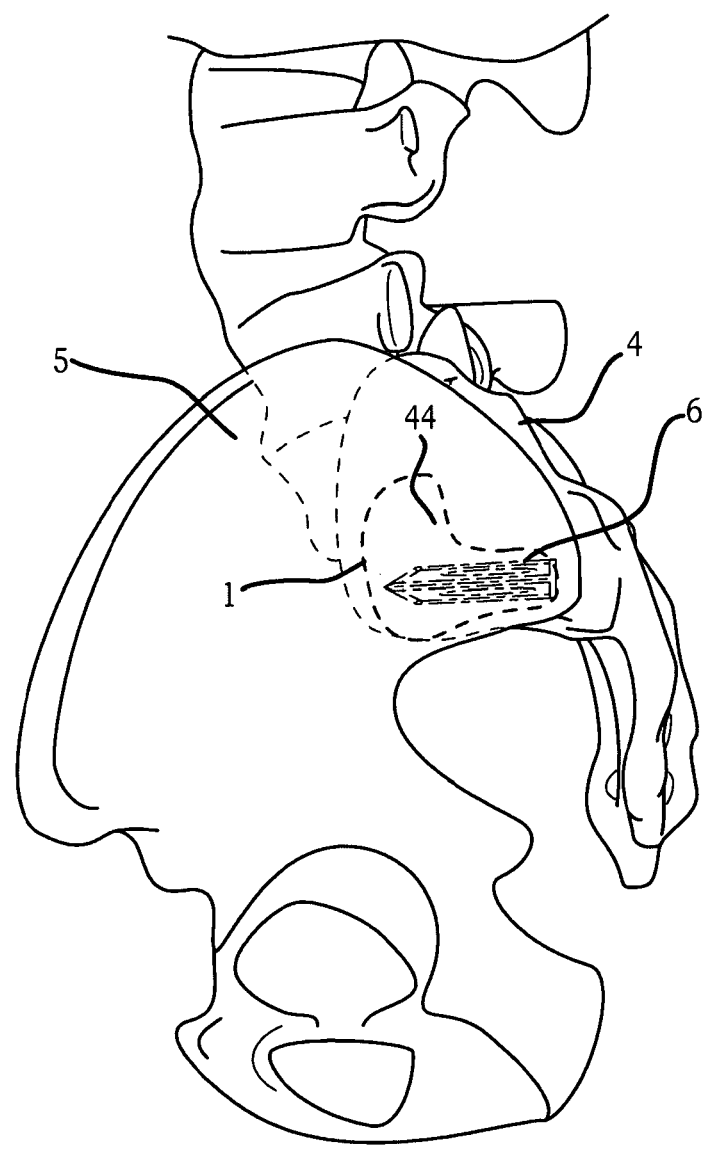
FIG. 22 provides a side view of the ilium with the articular surfaces of the sacroiliac joint and an embodiment of the fixation fusion implant located within the articular plane of the sacroiliac joint shown in broken line.
Figure 23:
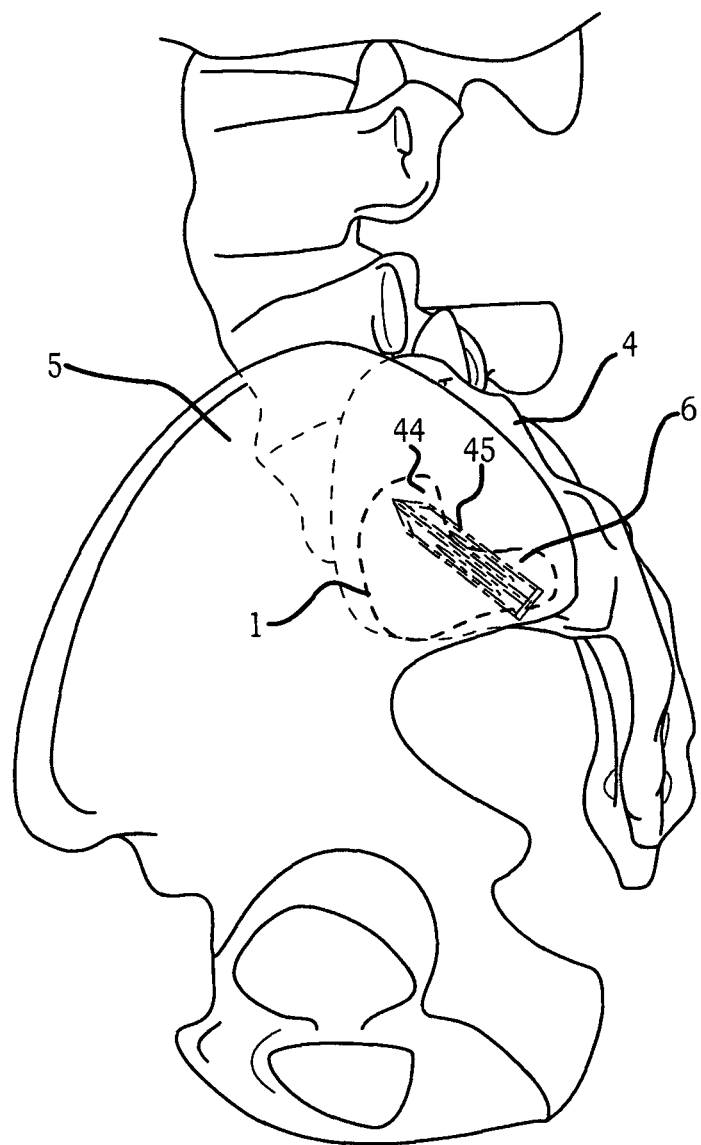
FIG. 23 provides a side view of the ilium with the articular surfaces of the sacroiliac joint and an embodiment of the fixation fusion implant located substantially within the articular plane of the sacroiliac joint and to a limited extent extra-articular of the sacroiliac joint shown in broken line.
Figure 24:
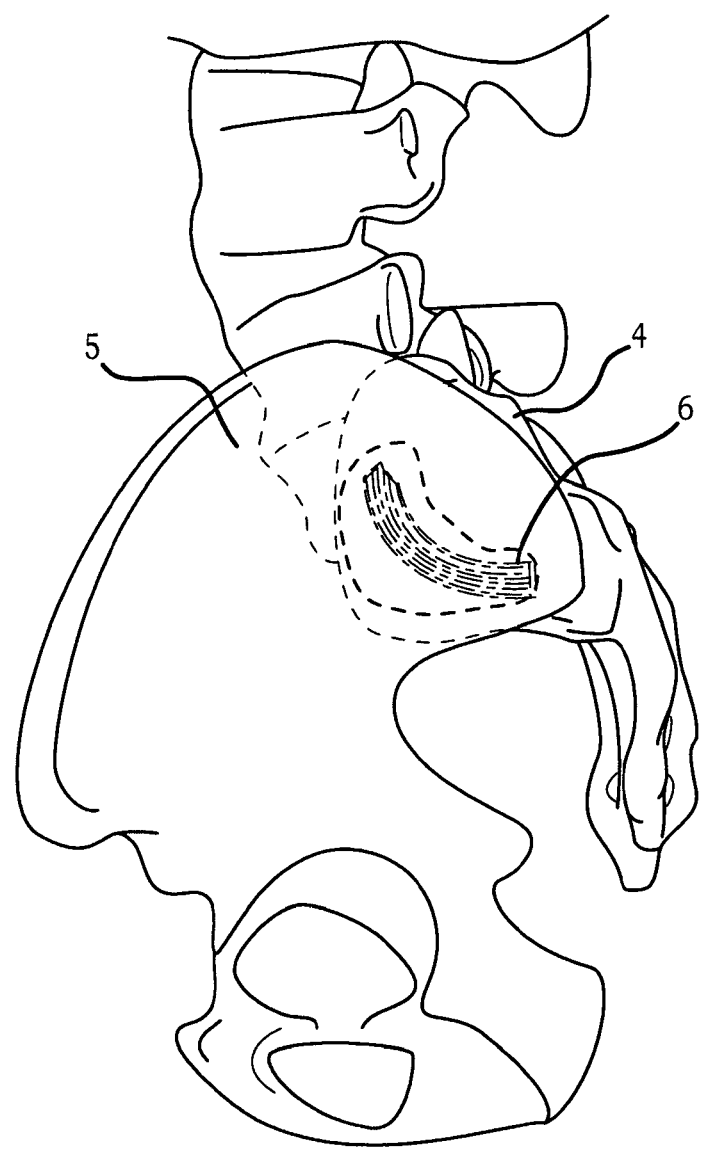
FIG. 24 provides a side view of the ilium with the articular surfaces of the sacroiliac joint and another embodiment of the fixation fusion implant located within the articular plane of the sacroiliac joint shown in broken line.

Now referring primarily to FIGS. 14-20, a non-limiting method of producing the implant receiving space (29) configured to receive various embodiments of the inventive fixation fusion device (6) within the articular plane (44) of the sacroiliac joint (1) (as shown within broken line of FIGS. 22, and 26) or in part within the articular plane (44) and in part the extra-articular plane (45) of the sacroiliac joint (1) (as shown by FIG. 23) is illustrated.

Figure 14:
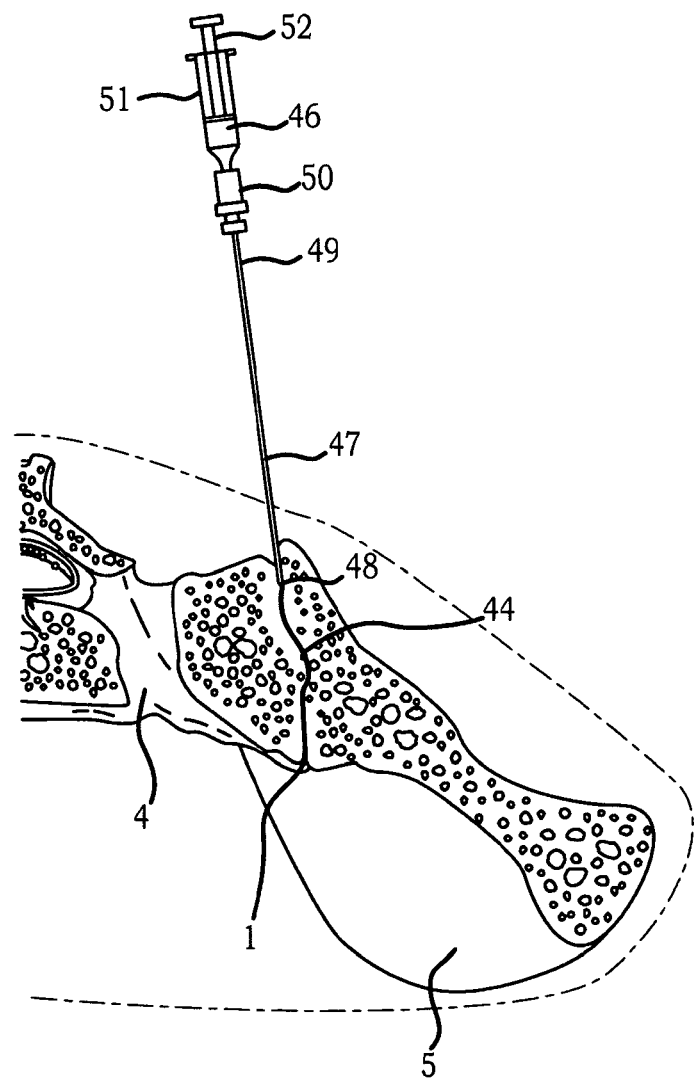
FIG. 14 is a cross section view through the sacroiliac joint which illustrates a method of implanting an embodiment of the fixation fusion implant the step including insertion of a needle into the articular plane of the sacroiliac joint to inject a radiographic dye to allow fluoroscopic visualization of the sacroiliac joint.

Now referring primarily to FIG. 14, an embodiment of the method can include the step of placing a patient under sedation prone on a translucent operating table (or other suitable surface). The sacroiliac joint can be locally anesthetized to allow for injecting a radiographic dye (46) (such as Isoview 300 radiographic contrast, or the like) under fluoroscopic guidance into the inferior aspect of the sacroiliac joint (1) to outline the lateral articular surface of the sacroiliac joint (1). Injection of the radiographic dye (46) within the sacroiliac joint (1) can be accomplished utilizing a tubular needle (47) having first needle end (48) which can be advanced into the sacroiliac joint (1) and having a second needle end (49) which removably couples to a hub (50). The hub (50) can be further configured to removably couple to a syringe barrel (51)(or other device for delivery of radiographic contrast). In the example of a syringe barrel (51), the syringe barrel (51) can have an internal volume capable of receiving an amount of the radiographic dye (46) sufficient for outlining the lateral articular surface of the sacroiliac joint (1). A plunger (52) can be slidingly received within the barrel (51) to deliver the radiographic dye (46) through the tubular needle (47) into the sacroiliac joint (1). The tubular needle (47) can have a gauge in the range of between about 16 gauge and about 20 gauge and can further be incrementally marked on the external surface to allow determination of the depth at which the first needle end (48) has advanced within the sacroiliac joint (1). As the first needle end (48) advances into the sacroiliac joint (1) the radiographic dye (46) can be delivered from within the syringe barrel (51) into the sacroiliac joint (1) to allow visualization of the sacroiliac joint (1) and location of the tubular needle (47) within the sacroiliac joint (1).

Figure 15:
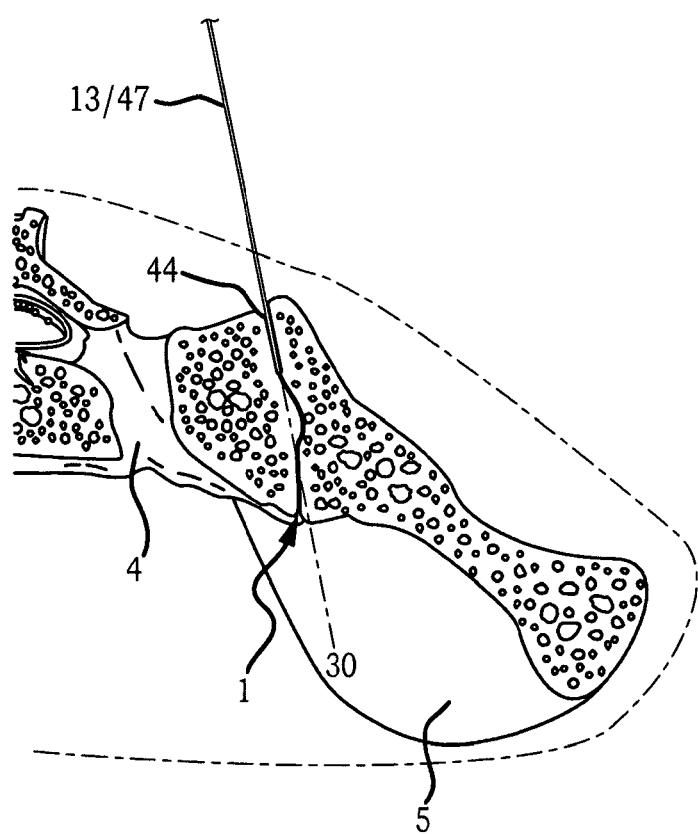
FIG. 15 is a cross section view through the sacroiliac joint which illustrates a method of implanting an embodiment of the fixation fusion implant the step including fixing the tubular needle within the sacroiliac joint as a guide wire.

Now referring primarily to FIG. 15, once the first needle end (48) has been sufficiently advanced into the sacroiliac joint (1) and the lateral articular surface of the sacroiliac joint (1) has been sufficiently visualized, the hub (50) can be removed from the tubular needle (47) leaving the tubular needle (47) fixed within the sacroiliac joint (1) as a initial guide for the tools subsequently used in removal of degenerative portions of the sacroiliac joint (1) and for production of the implant receiving space (29). Alternately, a guide wire (13) can be inserted along substantially the same path of the tubular needle (47) for fixed engagement within the sacroiliac joint (1) and used in subsequent steps as a guide.

Figure 16:
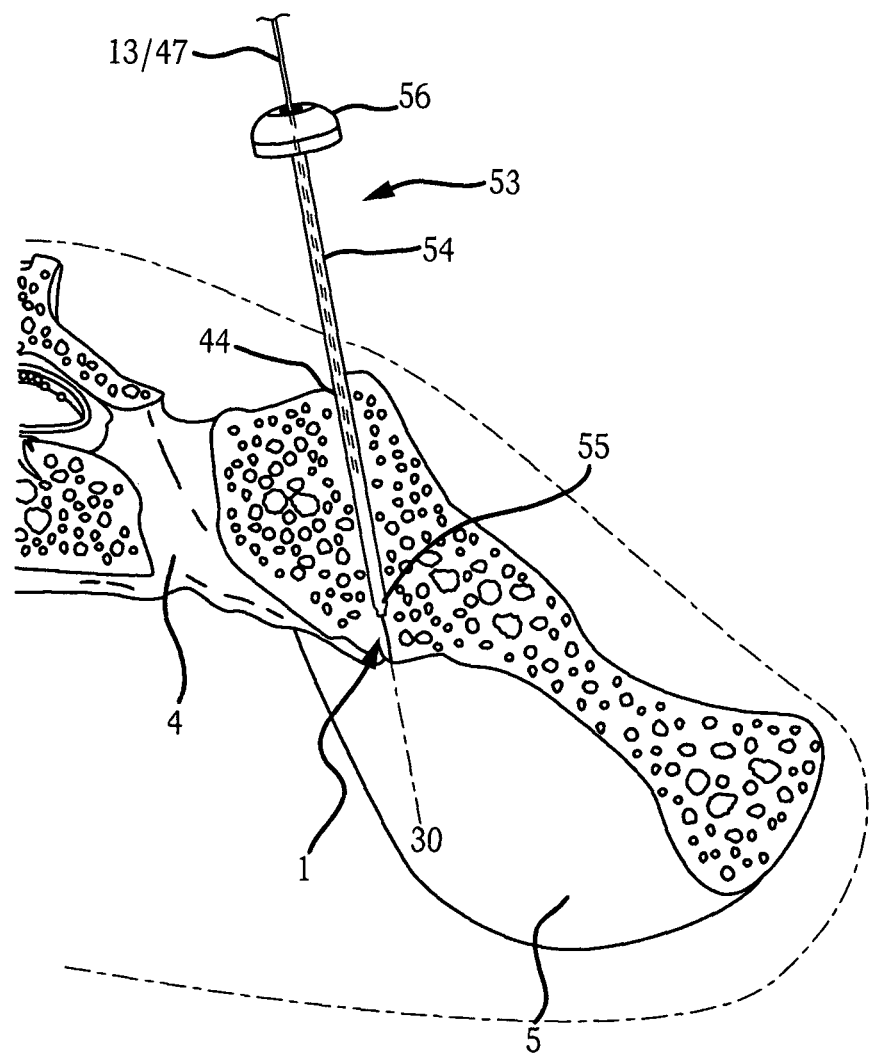
FIG. 16 is a cross section view through the sacroiliac joint which illustrates a method of implanting an embodiment of the fixation fusion implant the step including advancing a body of a cannulated probe along the needle fixed in the sacroiliac joint to fixed location at the anterior portion of the sacroiliac joint.

Again referring primarily to FIG. 16, a small incision can be made in the skin at the posterior superior (or as to certain embodiments inferior) aspect of the sacroiliac joint (1), extending proximal and distal to the tubular needle (47) along the line of the sacroiliac joint (1). A cannulated probe (53) can be slidingly engaged with the tubular needle (47)(or guide wire (13)) extending outwardly from the sacroiliac joint (1) (while the sacroiliac joint may be shown in the figures as being substantially linear for illustrative purposes, it is to be understood that the normal irregular features of the sacroiliac joint have not been removed). The cannulated probe (53) can have a probe body (54) of generally cylindrical shape terminating in a spatulate tip (55) at the end advanced into the sacroiliac joint (1). A removable cannulated probe handle (56) couples to the opposed end of the probe body (54). The spatulate tip (55) can be guided along the tubular needle (47)(or guide wire (13) into the posterior portion of the articular sacroiliac joint (1) and advanced to the anterior portion of the sacroiliac joint (1) under lateral fluoroscopic visualization. The cannulated probe handle (56) can then be removed providing the generally cylindrical probe body (54) extending outwardly from the sacroiliac joint (1) through the incision made in the skin.

Figure 17:
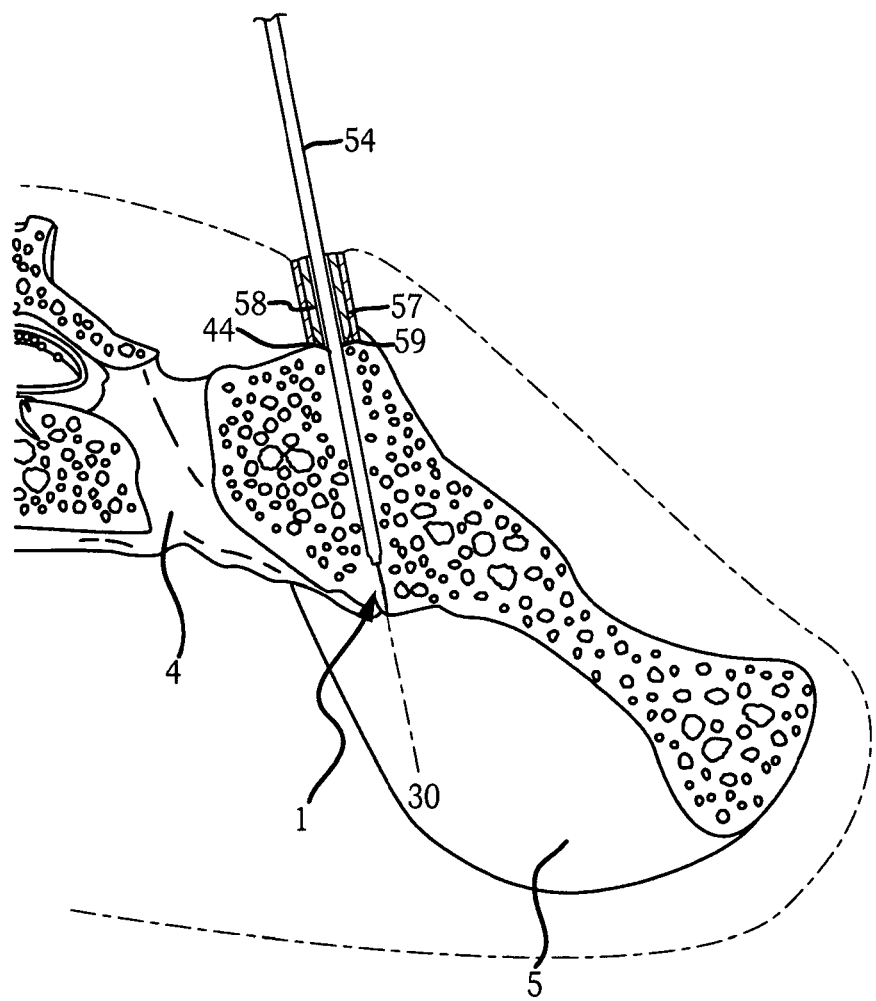
FIG. 17 is a cross section view through the sacroiliac joint which illustrates a method of implanting an embodiment of the fixation fusion implant the step including advancing a tissue dialator along the body of the cannulated probe fixed in the sacroiliac joint to allow placement of a access tube against the surface of the sacrum and ilium to expose the sacroiliac joint.

Now referring primarily to FIG. 17, an access tube (57) having inserted within a soft tissue dilator (58) having a blunt end (59) can be advanced over the probe body (54) until the blunt end (59) of the soft tissue dialator (58) and the corresponding end of the access tube (57) contact the posterior aspect of the sacroiliac joint (1). The soft tissue dialator (58) can be removed from within the access tube (57). The external surface of the access tube (57) sufficiently engaged with the surrounding tissue to avoid having the tissue locate with in the hollow inside of the access tube (57).

Figure 18:
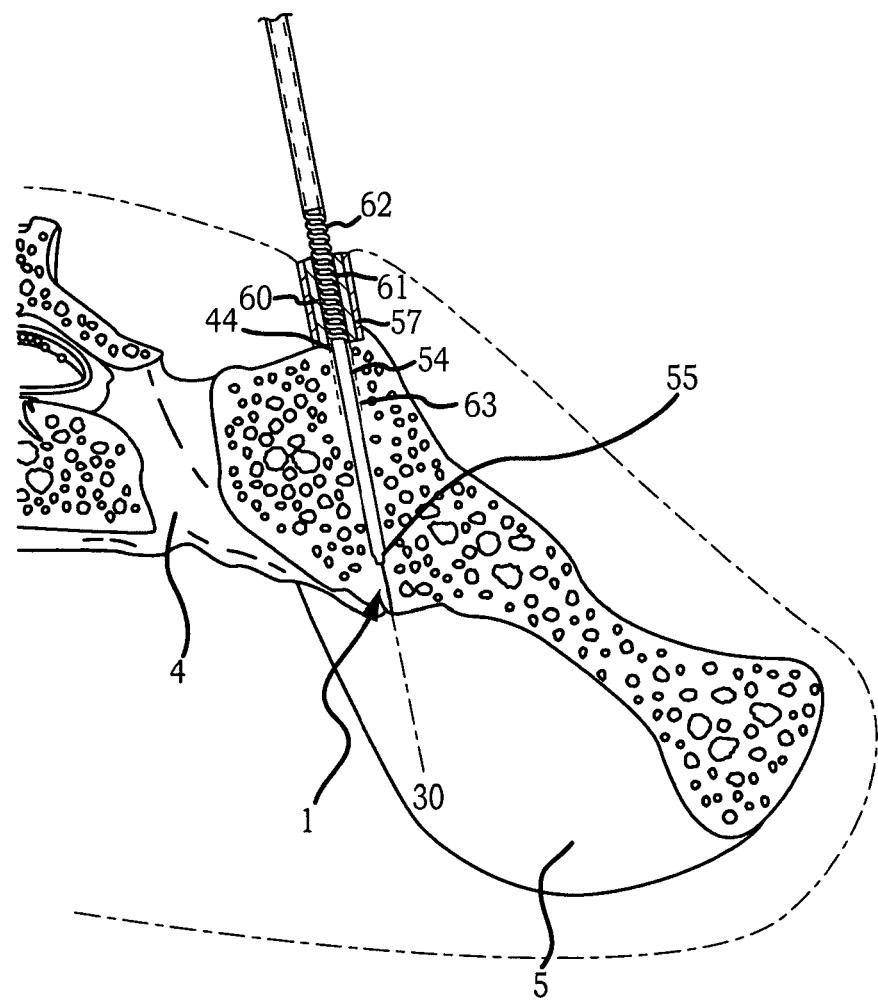
FIG. 18 is a cross section view through the sacroiliac joint which illustrates a method of implanting an embodiment of the fixation fusion implant the step including replacement of the tissue dialator with a first drill jig which receives a cannulated drill for production of a first bore hole substantially along the articular plane of the sacroiliac joint.

Now referring to FIG. 18, a first drill jig (60) can be advanced over the probe and received within the access tube (57). The probe body (54)(or guide wire (13)) extending outwardly from the sacroiliac joint (1) passes through a drill guide hole (61) of the first drill jig (60). A cannulated drill bit (62) can be advanced over the probe body (54) and within the drill guide hole (61) of the first drill jig (60). The cannulated drill bit (62) can be advanced into the sacroiliac joint (1) under fluoroscopic guidance to produce a first bore (63)(shown in broken line) within the sacroiliac joint (1) to a determined depth to remove a corresponding amount of cartilage from within the sacroiliac joint (1).

Figure 19:
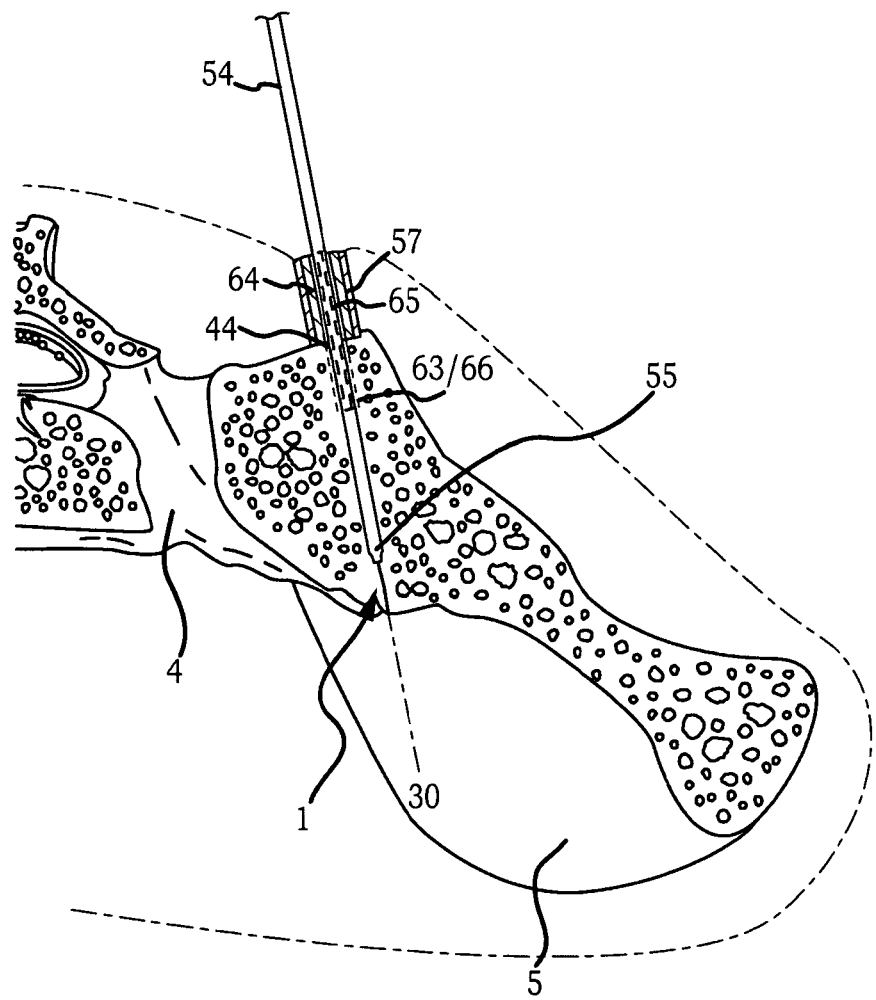
FIG. 19 is a cross section view through the sacroiliac joint which illustrates a method of implanting an embodiment of the fixation fusion implant the step including replacement of the first drill jig with a second drill jig which allows additional bore holes to be produced in relation to the first bore hole each substantially along the articular plane of the sacroiliac joint.

Now referring to FIG. 19, as to certain embodiments of the invention, the first drill jig (60) can be removed from within the access tube (57) and a second drill jig (64) can be advanced over the probe body (54) and received within the access tube (57); however, the invention is not limited to any particular number of drill jigs and as to certain embodiments of the method the first drill jig (60) can include all the required drill guide hole(s) (61)(65) and as to other embodiments of the method a plurality of drill jigs can be utilized in serial order to provide all the drill guide holes (61)(65). As the particular embodiment of the invention shown by the Figures, the second drill jig (64) can provide one or more additional drill guide holes (65) which locate in relation to the first bore (63) to allow a second or more cannulated drills (62) to be inserted within and advanced into the sacroiliac joint (1) to produce a second bore (66)(generally shown in broken line as 63/65) or a plurality of bores within the sacroiliac joint (1) spaced apart in predetermined pattern to allow removal of sufficient cartilage from the sacroiliac joint (1) for placement of embodiments of the fixation fusion implant (6).

Figure 20:
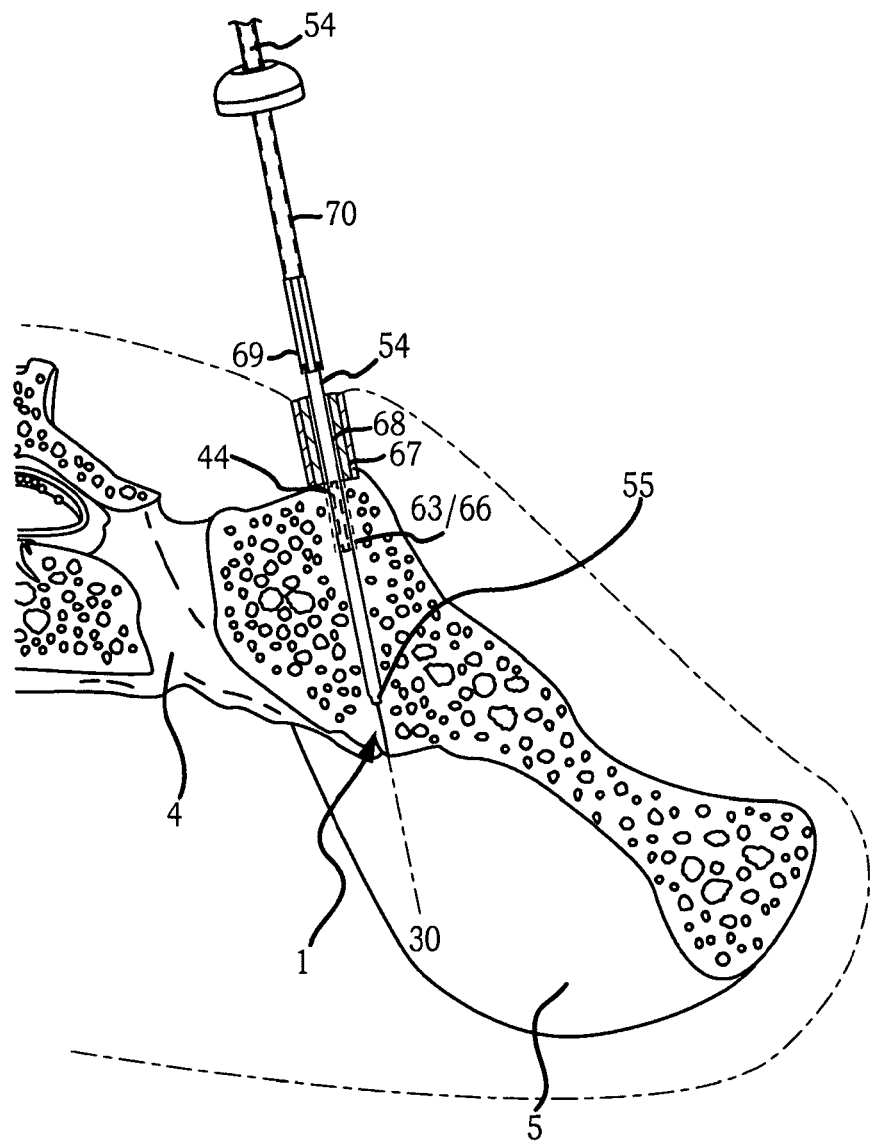
FIG. 20 is a cross section view through the sacroiliac joint which illustrates a method of implanting an embodiment of the fixation fusion implant the step including replacement of the second drill jig (or the first drill jig depending on the method) with a broach jig which receives a cannulated broach which can be advanced into the sacroiliac joint to produce an implant receiving space.

Now referring primarily to FIG. 20, in a subsequent step, the last in the serial presentation of drill jigs is removed from within the access tube (57) and a broach jig (67) can be advanced over the probe body (54) to locate within the access tube (57). The broach jig (67) can include a broach guide hole (68) which receives a first broach end (69) of a cannulated broach (70) advanced over the probe body (54). The first broach end (69) can have a configuration which can be advanced into the sacroiliac joint (1) to remove a further amount of cartilage from the sacroiliac joint (1). The cannulated broach (70) can remove cartilage from within the sacroiliac joint (1) sufficient to produce a suitable implant receiving space (29) configured as above described to receive embodiments of the fixation fusion implant (6).

Figure 21A:
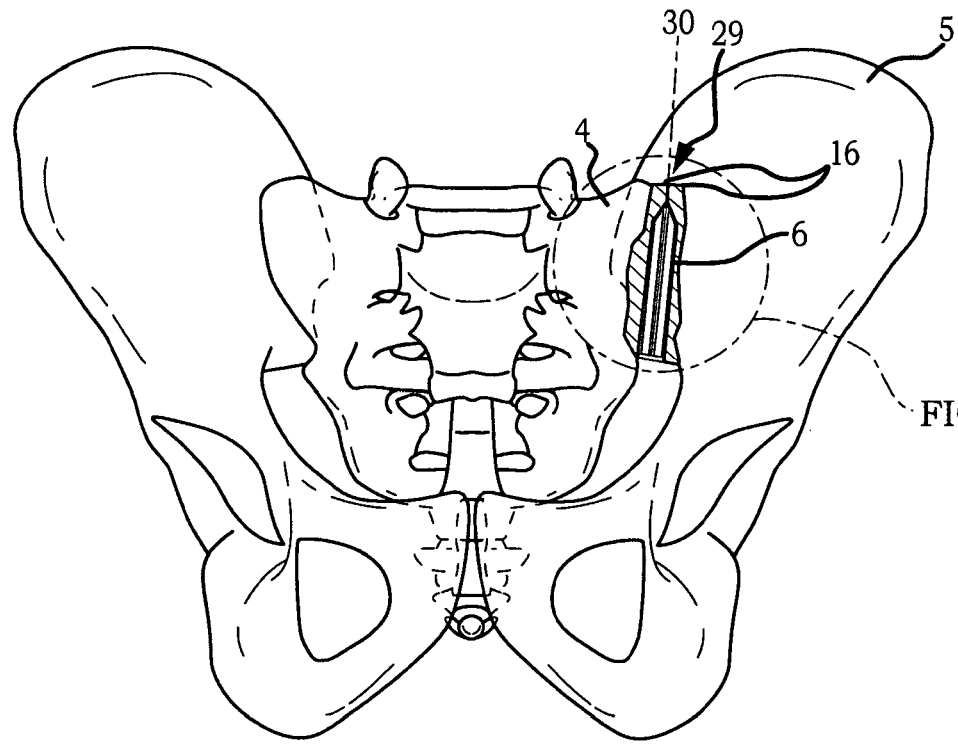
FIG. 21A provides a cutaway view of the sacroiliac joint showing placement of a particular embodiment of the fixation fusion implant in the implant receiving space produced by the method illustrated in FIGS. 14-20.
Figure 21B:
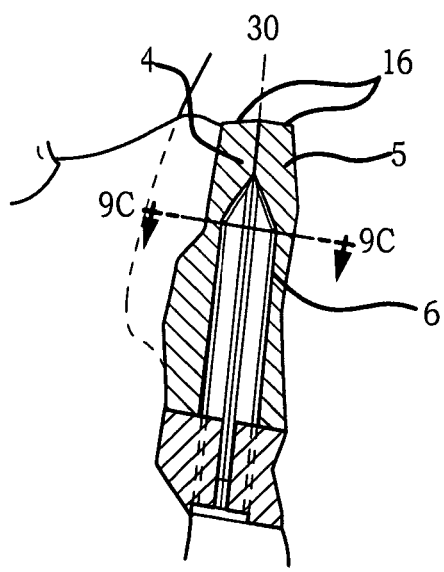
FIG. 21B is an enlarged view of a portion of FIG. 21A showing placement of a particular embodiment of the fixation fusion implant in the implant receiving space produced by the method illustrated in FIGS. 14-20.
Figure 21C:
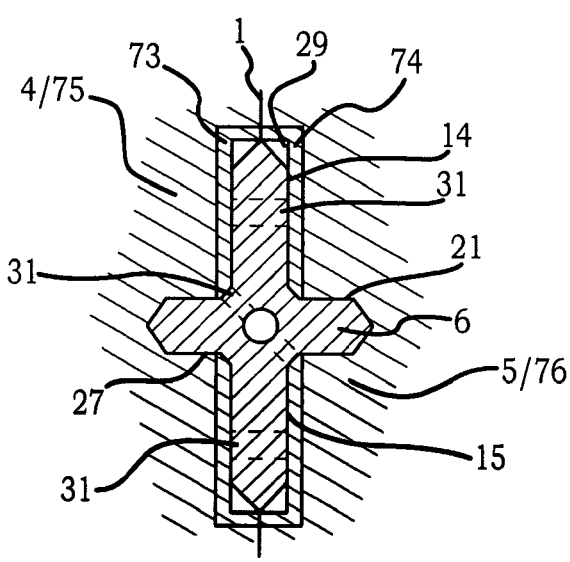
FIG. 21C is a cross section view 9C-9C shown in FIG. 21B which shows the configuration of the implant receiving space produced by the method illustrated in FIGS. 14-20 and a particular embodiment of the fixation fusion implant implanted therein implanted.

Now referring primarily to FIGS. 21A, 21B, and 21C, the implant receiving space (29) can have a final configuration which allows at least a portion of the external surface of the first radial member (14) and the second radial member (15) to engage a portion of the cortical bone (74) of the ilium (5) and at least a portion of the external surface of the first radial member (14) and the second radial member (15) to engage a portion of the cortical bone (73) of the sacrum (4). As to those embodiments of the fixation fusion implant (6) which have a third radial member (26) and a fourth radial member (27), impact of the fixation fusion implant (6) into the implant receiving space (29) forcibly urges the radial members (26)(27) into the cancellous bone (75)(76) of the sacrum (4) and the ilium (5) respectively. Mechanical fasteners (39)(such as treaded members) can be inserted through the bores (36) in the anti-migration element (33) and into the sacrum (4) and ilium (5) to fix location of the fixation fusion implant (6) within the implant receiving space (29).

Example 1

An embodiment of the inventive fixation fusion implant having a configuration substantially as shown by FIGS. 3-6 and as above-described was inserted by methods as substantially above described into a patient under direct visualization and with assisted lateral fluoroscopy. The procedure was performed for the purpose of assessing in an actual reduction to practice the ability of the inventive fixation fusion implant to be safely implanted into the inferior portion of the sacroiliac joint substantially and to confirm the that implantation of the fixation fusion device into a implant receiving space configured substantially as above-described acts to immobilize the sacroiliac joint. The fixation fusion implant as above-described implanted into the inferior portion of the sacroiliac joint proved to immediately immobilize the sacroiliac joint. The embodiment of the fixation fusion device was then removed and the joint was fused with a conventional open fusion technique. The implantation method and implantation of the embodiment of the fixation fusion implant was documented by fluoroscopic imaging.

As can be easily understood from the foregoing, the basic concepts of the present invention may be embodied in a variety of ways. The invention involves numerous and varied embodiments of sacroiliac joint fusion system which includes fixation fusion implants and methods of implanting the fixation fusion implants to provide fixation and fusion of the sacroiliac joint.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "an implant" should be understood to encompass disclosure of the act of "implanting"— whether explicitly discussed or not—and, conversely, were there effectively disclosure of the act of "implanting", such a disclosure should be understood to encompass disclosure of "an implant" and even a "means for implanting a member." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. Moreover, the term "about" means as to any numeric value a deviation about that numeric value of up to ten percent.

Moreover, for the purposes of the present invention, the term "a" or "an" entity refers to one or more of that entity; for example, "a member" or "an elongate member" refers to one or more member(s) or at least one member. As such, the terms "a" or "an", "one or more" and "at least one" can be used interchangeably herein.

Thus, the applicant(s) should be understood to claim at least: i) a fixation fusion implant as herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method for preparing a sacroiliac joint for stabilization, the sacroiliac joint defined between a sacrum and an ilium, the ilium comprising a posterior superior iliac spine (PSIS) and a posterior inferior iliac spine (PIIS), the sacroiliac joint comprising an articular plane defined by an articular boundary, and an extra-articular plane outside the articular boundary, the articular boundary defining an anterior boundary segment at an anterior portion of the articular plane, and a posterior boundary segment at a posterior portion of the articular plane, the articular boundary comprising a superior-posterior corner and an inferior-posterior corner at the posterior portion, the method comprising:
    approaching a posterior aspect of the sacroiliac joint with a defect-creating tool assembly comprising a drill bit and a jig comprising first and second drill guide holes configured to guide the drill bit along first and second trajectories, respectively;
    creating a defect in the sacrum and the ilium by delivering the drill bit into the sacrum and the ilium via guidance by the first and second drill guide holes of the jig, the defect having a shape defined by at least one noncircular cross-sectional shape in a plane generally perpendicular to a joint plane of the sacroiliac joint; and
    delivering an implant into the sacroiliac joint, the implant comprising a first portion of an exterior surface configured to generally match the at least one noncircular cross-sectional shape of the defect created by the defect-creating tool assembly.

2. The method of claim 1, wherein the noncircular cross sectional shape in the plane generally perpendicular to the joint plane of the sacroiliac joint comprises a rectangular shape that bridges across the sacroiliac joint and into the sacrum and the ilium.

3. The method of claim 1, wherein the first portion of the exterior surface of the implant is defined on a first member of the implant that is generally planar.

4. The method of claim 3, wherein the implant further comprises a second member having a second portion of the exterior surface of the implant, the second member comprising a sacral end and an iliac end opposite each other, the sacral end of the second member protruding from a sacral side of the first member, the iliac end of the second member protruding from an iliac side of the first member.

5. The method of claim 4, wherein the first member is positioned centrally between the sacral end and iliac end of the second member.

6. The method of claim 4, wherein the second member is generally planar and oriented generally perpendicular to the first member.

7. The method of claim 1, wherein the implant further comprises an elongate body having a generally cylindrical cross-sectional shape that is transverse to a length of the implant, the elongate body coupled to the first member along at least a portion of the length.

8. The method of claim 7, wherein the elongate body is coupled to the first member at a midpoint thereof such that the first member protrudes from opposite sides of the elongate body.

9. The method of claim 1, wherein creating the defect in the sacrum and the ilium is performed via fluoroscopic guidance.

10. The method of claim 1, wherein the defect-creating tool assembly comprises a plurality of jigs comprising the jig and another jig, and wherein creating the defect in the sacrum and ilium comprises using the another jig from the plurality of jigs to guide a cutting tool selected from the drill bit and an instrument having a chisel tip.

11. The method of claim 10, wherein the jig comprises the first drill hole in a first location, and the another jig comprises a second cutting tool hole in a second location that is different than the first location.

12. The method of claim 1, wherein, in delivering the implant into the sacroiliac joint, the implant passes through an access region defined between the PSIS and PITS.

13. The method of claim 1, wherein, in delivering the implant into the sacroiliac joint, the implant passes through an access region defined between the superior-posterior corner and the inferior-posterior corner at the posterior portion of the articular boundary.

14. A method for preparing a sacroiliac joint for stabilization, the sacroiliac joint defined between a sacrum and an ilium, the ilium comprising a posterior superior iliac spine (PSIS) and a posterior inferior iliac spine (PIIS), the sacroiliac joint comprising an articular plane defined by an articular boundary, and an extra-articular plane outside the articular boundary, the articular boundary defining an anterior boundary segment at an anterior portion of the articular plane, and a posterior boundary segment at a posterior portion of the articular plane, the articular boundary comprising a superior-posterior corner and an inferior-posterior corner at the posterior portion, the method comprising:
  approaching a posterior aspect of the sacroiliac joint with a defect-creating tool assembly comprising a cutting tool, the cutting tool having a distal end and proximal end opposite thereof and an axis extending therebetween;
  aligning the axis of the cutting tool generally parallel with a plane of the sacroiliac joint;
  creating a defect at the sacroiliac joint via the cutting tool contacting at least one of the sacrum, the ilium, and the sacroiliac joint with the axis of the cutting tool generally parallel with the plane of the sacroiliac joint, the defect having a shape defined by at least one noncircular cross-sectional shape in a plane generally perpendicular to the joint plane of the sacroiliac joint; and
  delivering an implant into the sacroiliac joint such that a first portion of an exterior surface of the implant is at least partially received within the defect, the first portion of the exterior surface of the implant having a cross-sectional shape that generally matches the at least one noncircular cross-sectional shape of the defect, the implant further comprising a second portion of the exterior surface that extends outward from the first portion and into the sacrum and the ilium, respectively, beyond the defect generally matching the first portion of the exterior surface of the implant.

15. The method of claim 14, wherein the second portion is connected to the first portion and has a cross-sectional geometry which is different from the cross-sectional geometry of the first portion.

16. The method of claim 14, wherein, when the first portion of the exterior surface of the implant is at least partially received within the defect, the second portion bridges across the sacroiliac joint.

17. The method of claim 14, wherein, when the first portion of the exterior surface of the implant is at least partially received within the defect, the second portion extends transversely to the joint plane of the sacroiliac joint.

18. The method of claim 14, wherein the defect-creating tool assembly further comprises a broach, and wherein creating the defect further comprises contacting the at least one of the sacrum, the ilium, and the sacroiliac joint with a distal end of the broach.

19. The method of claim 14, wherein the cutting tool comprises a drill.

20. The method of claim 19, wherein the defect-creating tool assembly further comprises a drill jig configured to guide advancement of the drill, and wherein the drill jig is used to align the axis of the cutting tool generally parallel with a plane of the sacroiliac joint.

21. The method of claim 14, wherein, in delivering the implant into the sacroiliac joint, the implant passes through an access region defined between the PSIS and PIIS.

22. The method of claim 14, wherein, in delivering the implant into the sacroiliac joint, the implant passes through an access region defined between the superior-posterior corner and the inferior-posterior corner at the posterior portion of the articular boundary.

23. A method for preparing a sacroiliac joint for stabilization, the sacroiliac joint defined between a sacrum and an ilium, the ilium comprising a posterior superior iliac spine (PSIS) and a posterior inferior iliac spine (PITS), the sacroiliac joint comprising an articular plane defined by an articular boundary, and an extra-articular plane outside the articular boundary, the articular boundary defining an anterior boundary segment at an anterior portion of the articular plane, and a posterior boundary segment at a posterior portion of the articular plane, the articular boundary comprising a superior-posterior corner and an inferior-posterior corner at the posterior portion, the method comprising:
  approaching a posterior aspect of the sacroiliac joint with a defect-creating tool assembly comprising a drill bit, and first and second jigs, the first jig comprising a first drill guide hole configured to guide the drill bit along a first trajectory, the second jig comprising a second drill guide hole configured to guide the drill bit along a second trajectory that is different than the first trajectory;
  creating a defect in the sacrum and the ilium by delivering the drill bit into the sacrum and the ilium via guidance by the first and second drill guide holes of the first and second jigs, respectively, the defect having a shape defined by at least one noncircular cross-sectional shape in a plane generally perpendicular to a joint plane of the sacroiliac joint; and
  delivering an implant into the sacroiliac joint, the implant comprising a first portion of an exterior surface configured to generally match the at least one noncircular cross-sectional shape of the defect created by the defect-creating tool assembly.

24. The method of claim 23, wherein the noncircular cross sectional shape in the plane generally perpendicular to the joint plane of the sacroiliac joint comprises a rectangular shape that bridges across the sacroiliac joint and into the sacrum and the ilium.

25. The method of claim 23, wherein the first portion of the exterior surface of the implant is defined on a first member of the implant that is generally planar.

26. The method of claim 25, wherein the implant further comprises a second member having a second portion of the exterior surface of the implant, the second member comprising a sacral end and an iliac end opposite each other, the sacral end of the second member protruding from a sacral side of the first member, the iliac end of the second member protruding from an iliac side of the first member.

27. The method of claim 26, wherein the first member is positioned centrally between the sacral end and iliac end of the second member.

28. The method of claim 26, wherein the second member is generally planar and oriented generally perpendicular to the first member.

29. The method of claim 23, wherein the implant further comprises an elongate body having a generally cylindrical cross-sectional shape that is transverse to a length of the implant, the elongate body coupled to the first member along at least a portion of the length.

30. The method of claim 29, wherein the elongate body is coupled to the first member at a midpoint thereof such that the first member protrudes from opposite sides of the elongate body.

31. The method of claim 23, wherein creating the defect in the sacrum and the ilium is performed via fluoroscopic guidance.

32. The method of claim 23, wherein, in delivering the implant into the sacroiliac joint, the implant passes through an access region defined between the PSIS and PIIS.

33. The method of claim 23, wherein, in delivering the implant into the sacroiliac joint, the implant passes through an access region defined between the superior-posterior corner and the inferior-posterior corner at the posterior portion of the articular boundary.

34. A method for preparing a sacroiliac joint for stabilization, the sacroiliac joint defined between a sacrum and an ilium, the ilium comprising a posterior superior iliac spine (PSIS) and a posterior inferior iliac spine (PITS), the sacroiliac joint comprising an articular plane defined by an articular boundary, and an extra-articular plane outside the articular boundary, the articular boundary defining an anterior boundary segment at an anterior portion of the articular plane, and a posterior boundary segment at a posterior portion of the articular plane, the articular boundary comprising a superior-posterior corner and an inferior-posterior corner at the posterior portion, the method comprising:
approaching a posterior aspect of the sacroiliac joint with a defect-creating tool assembly comprising a first cutting tool, a second cutting tool, and first and second cutting guides, the first cutting guide comprising a first cutting guide path configured to guide the first cutting tool along a first trajectory, the second cutting guide comprising a second cutting guide path configured to guide the second cutting tool along a second trajectory that is different than the first trajectory;
creating a defect in the sacrum and the ilium by delivering the first cutting tool and second cutting tool into at least one of the sacrum, the ilium, and sacroiliac joint via guidance by the first and second cutting guide holes of the first and second cutting guides, respectively; and
delivering an implant into the sacroiliac joint, the implant comprising a first portion of an exterior surface configured to generally match the cross-sectional shape of the defect created by the defect-creating tool assembly.

35. The method of claim 34, wherein the defect defines a non-circular cross-sectional shape in a plane generally perpendicular to a joint plane of the sacroiliac joint, and wherein the first portion of the exterior surface of the implant is non-circular.

36. The method of claim 34, wherein the first cutting tool is a drill bit and second cutting tool is a broach.

37. The method of claim 34, wherein, in implanting the implant into the sacroiliac joint via the posterior aspect, the implant passes through an access region defined between the superior-posterior corner and the inferior-posterior corner.

38. A method for preparing a sacroiliac joint for stabilization, the sacroiliac joint defined between a sacrum and an ilium, the method comprising:
approaching a posterior aspect of the sacroiliac joint with a defect-creating tool assembly comprising a first cutting tool, a second cutting tool, and first and second cutting guides, the first cutting guide comprising a first cutting guide path configured to guide the first cutting tool along a first trajectory, the second cutting guide comprising a second cutting guide path configured to guide the second cutting tool;
creating a defect in the sacrum and the ilium by delivering the first cutting tool and second cutting tool into at least one of the sacrum, the ilium, and sacroiliac joint via guidance by the first and second cutting guide paths of the first and second cutting guides, respectively, the defect having a shape defined by a cross-sectional shape in a plane generally perpendicular to a joint plane of the sacroiliac joint; and
delivering an implant into the sacroiliac joint, the implant comprising a body extending a length between a proximal end and a distal end, and comprising a longitudinal axis, a first, second, third and fourth members extending along the length generally outwardly from the longitudinal axis, and separated by one another by a first, second, third and fourth angles, the body of the implant further comprising a first portion of an exterior surface configured to generally match the cross-sectional shape of the defect created by the defect-creating tool assembly.

39. The method of claim 38, wherein the first, second, third and fourth members are generally planar members.

40. The method of claim 38, wherein the first, second, third and fourth angles are generally each about 90 degrees.

41. The method of claim 38, wherein each pair of the first and third members, and the second and fourth members are mirror images of each other, and are arranged in a mirrored position relative to the longitudinal axis.

42. A method for preparing a sacroiliac joint for stabilization, the sacroiliac joint defined between a sacrum and an ilium, the method comprising:
approaching a posterior aspect of the sacroiliac joint with a defect-creating tool assembly comprising a first cutting tool and a first cutting guide, the first cutting guide comprising a first cutting guide path configured to guide the first cutting tool along a first trajectory;
creating a defect in the sacrum and the ilium by delivering the first cutting tool into at least one of the sacrum, the ilium, and sacroiliac joint via guidance by the first cutting guide path of the first cutting guide, respectively, the defect having a shape defined by a cross-sectional shape in a plane generally perpendicular to a joint plane of the sacroiliac joint; and
delivering an implant into the sacroiliac joint, the implant comprising a body extending a length between a proximal end and a distal end, and having a generally rectangular volume including a sacral side opposite an iliac side, a top side opposite a bottom side, an opening extending between the top and bottom sides, and first and second passages extending through the proximal end, wherein a location of the first passage is positioned adjacent the sacrum and a location of the second passage is positioned adjacent the ilium, and a first portion of an exterior surface configured to generally match the cross-sectional shape of the defect created by the defect-creating tool assembly; and delivering a first elongate member into engagement with the sacrum while supported by the first passage, and delivering a second elongate member into engagement with the ilium while supported by the second passage.

\* \* \* \* \*

UNITED STATES PATENT AND TRADEMARK OFFICE
CERTIFICATE OF CORRECTION

PATENT NO. : 10,517,734 B2
APPLICATION NO. : 16/041372
DATED : December 31, 2019
INVENTOR(S) : Donner It is certified that error appears in the above-identified patent and that said Letters Patent is hereby corrected as shown below:

In the Claims

Claim 12, Column 19, Line 21, delete "PITS" and replace with --PIIS--.

Claim 23, Column 20, Line 33, delete "(PITS)" and replace with --(PIIS)--.

Claim 34, Column 21, Line 41, delete "(PITS)" and replace with --(PIIS)--.

Signed and Sealed this
Twenty-eighth Day of April, 2020

Andrei Iancu
*Director of the United States Patent and Trademark Office*